US010586254B2

(12) United States Patent
Singhal

(10) Patent No.: US 10,586,254 B2
(45) Date of Patent: Mar. 10, 2020

(54) METHOD AND SYSTEM FOR ADAPTIVE VEHICLE CONTROL IN AUTONOMOUS VEHICLES

(71) Applicant: NIO USA, Inc., San Jose, CA (US)

(72) Inventor: Abhishek Singhal, Santa Clara, CA (US)

(73) Assignee: NIO USA, Inc., San Jose, CA (US)

( * ) Notice: Subject to any disclaimer, the term of this patent is extended or adjusted under 35 U.S.C. 154(b) by 198 days.

(21) Appl. No.: 15/415,650

(22) Filed: Jan. 25, 2017

(65) Prior Publication Data
US 2018/0141562 A1    May 24, 2018

Related U.S. Application Data

(60) Provisional application No. 62/424,976, filed on Nov. 21, 2016.

(51) Int. Cl.
*G06Q 30/02* (2012.01)
*G06F 16/29* (2019.01)
(Continued)

(52) U.S. Cl.
CPC .......... *G06Q 30/0266* (2013.01); *A61B 5/01* (2013.01); *A61B 5/024* (2013.01); *A61B 5/08* (2013.01); *A61B 5/165* (2013.01); *A61B 5/18* (2013.01); *B60R 11/04* (2013.01); *B60S 1/62* (2013.01); *B60W 10/04* (2013.01); *B60W 10/18* (2013.01); *B60W 10/20* (2013.01); *B60W 30/09* (2013.01); *B60W 40/04* (2013.01); *B60W 40/08* (2013.01); *B60W 40/09* (2013.01); *B60W 40/105* (2013.01); *B60W 50/0097* (2013.01); *B60W 50/0098* (2013.01); *B60W 50/08* (2013.01); *B60W 50/082* (2013.01); *B62D 15/00* (2013.01); *B62D 15/0265* (2013.01); *G01C 21/3407* (2013.01); *G01C 21/3461* (2013.01); *G01C 21/3469* (2013.01); *G01C 21/3484* (2013.01); *G01C 21/3492* (2013.01);
(Continued)

(58) Field of Classification Search
CPC .. B60W 50/14; B60W 50/00; B60W 50/0097; B60W 50/087; B60W 50/0098; B60W 50/12; B60W 40/09; B60W 10/18; B60W 50/10; G06Q 30/0266; G06F 16/95; G06F 16/29; A61B 5/01; G05D 1/0088
See application file for complete search history.

(56) References Cited

U.S. PATENT DOCUMENTS 9,229,905 B1 *  1/2016 Penilla .................... G06F 17/00
9,701,316 B2 *  7/2017 Jelbert .................. B60W 40/09
(Continued)

OTHER PUBLICATIONS

Kautonen, "NextEV unveils the NIO EP9 electric supercar in London," Autoblog, 2016, retrieved from http://www.autoblog.com/2016/11/21/nextev-unveiles-the-nio-ep9-electric-supercar-in-london/, 4 pages.
(Continued)

*Primary Examiner* — Hunter B Lonsberry
*Assistant Examiner* — Luis A Martinez Borrero
(74) *Attorney, Agent, or Firm* — Sheridan Ross P.C.

(57) ABSTRACT

Systems of an electrical vehicle and the operations thereof are provided that use object profiles to select autonomous vehicle operations, including acceleration rate, deceleration rate, steering angle, and inter-vehicle spacing.

21 Claims, 12 Drawing Sheets

(51) Int. Cl.

| | |
|---|---|
| G01S 13/86 | (2006.01) |
| G01S 15/02 | (2006.01) |
| G08G 1/16 | (2006.01) |
| G06F 16/95 | (2019.01) |
| B62D 15/02 | (2006.01) |
| G01C 21/34 | (2006.01) |
| G01S 13/87 | (2006.01) |
| G01C 21/36 | (2006.01) |
| B60R 11/04 | (2006.01) |
| B60S 1/62 | (2006.01) |
| G01S 7/40 | (2006.01) |
| G01S 7/497 | (2006.01) |
| G01S 17/89 | (2006.01) |
| G02B 27/00 | (2006.01) |
| B60W 30/09 | (2012.01) |
| B60W 50/00 | (2006.01) |
| G05D 1/00 | (2006.01) |
| G05D 1/02 | (2006.01) |
| A61B 5/01 | (2006.01) |
| A61B 5/024 | (2006.01) |
| A61B 5/08 | (2006.01) |
| A61B 5/16 | (2006.01) |
| A61B 5/18 | (2006.01) |
| B60W 40/09 | (2012.01) |
| B60W 50/08 | (2020.01) |
| B60W 10/18 | (2012.01) |
| B60W 10/20 | (2006.01) |
| B60W 10/04 | (2006.01) |
| B60W 40/04 | (2006.01) |
| B60W 40/08 | (2012.01) |
| B60W 40/105 | (2012.01) |
| B62D 15/00 | (2006.01) |
| G01S 13/931 | (2020.01) |
| G01S 13/93 | (2020.01) |

(52) U.S. Cl.
CPC ..... *G01C 21/3682* (2013.01); *G01C 21/3691* (2013.01); *G01C 21/3697* (2013.01); *G01S 7/4021* (2013.01); *G01S 7/497* (2013.01); *G01S 13/862* (2013.01); *G01S 13/865* (2013.01); *G01S 13/867* (2013.01); *G01S 13/87* (2013.01); *G01S 15/02* (2013.01); *G01S 17/89* (2013.01); *G02B 27/0006* (2013.01); *G05D 1/0061* (2013.01); *G05D 1/0088* (2013.01); *G05D 1/0212* (2013.01); *G05D 1/0214* (2013.01); *G05D 1/0221* (2013.01); *G05D 1/0276* (2013.01); *G06F 16/29* (2019.01); *G06F 16/95* (2019.01); *G06Q 30/0269* (2013.01); *G08G 1/161* (2013.01); *G08G 1/163* (2013.01); *G08G 1/164* (2013.01); *G08G 1/165* (2013.01); *G08G 1/166* (2013.01); *B60W 2040/0809* (2013.01); *B60W 2050/0004* (2013.01); *B60W 2050/0014* (2013.01); *B60W 2300/34* (2013.01); *B60W 2510/08* (2013.01); *B60W 2510/18* (2013.01); *B60W 2520/04* (2013.01); *B60W 2520/105* (2013.01); *B60W 2540/18* (2013.01); *B60W 2540/22* (2013.01); *B60W 2540/28* (2013.01); *B60W 2540/30* (2013.01); *B60W 2550/10* (2013.01); *B60W 2550/30* (2013.01); *B60W 2710/18* (2013.01); *B60W 2710/20* (2013.01); *B60W 2750/40* (2013.01); *B60W 2900/00* (2013.01); *G01S 2007/4043* (2013.01); *G01S 2007/4977* (2013.01); *G01S 2013/935* (2013.01); *G01S 2013/936* (2013.01); *G01S 2013/9325* (2013.01); *G01S 2013/9342* (2013.01); *G01S 2013/9346* (2013.01); *G01S 2013/9353* (2013.01); *G01S 2013/9357* (2013.01); *G01S 2013/9375* (2013.01); *G01S 2013/9378* (2013.01); *G01S 2013/9382* (2013.01); *G01S 2013/9385* (2013.01); *G01S 2013/9389* (2013.01); *G05D 2201/0212* (2013.01)

(56) References Cited

U.S. PATENT DOCUMENTS

| | | | |
|---|---|---|---|
| 10,031,523 B2* | 7/2018 | Ricci | B60R 25/2018 |
| 2012/0083960 A1* | 4/2012 | Zhu | G05D 1/0214 |
| | | | 701/23 |
| 2012/0317161 A1* | 12/2012 | Bai | G06F 16/435 |
| | | | 709/201 |
| 2014/0195113 A1 | 7/2014 | Lu et al. | |
| 2016/0209220 A1* | 7/2016 | Laetz | G08G 1/202 |
| 2017/0136880 A1 | 5/2017 | Ricci | |
| 2017/0136881 A1 | 5/2017 | Ricci | |
| 2017/0136882 A1 | 5/2017 | Ricci | |
| 2017/0136885 A1 | 5/2017 | Ricci | |
| 2017/0136887 A1 | 5/2017 | Ricci | |
| 2017/0136888 A1 | 5/2017 | Ricci | |
| 2017/0136889 A1 | 5/2017 | Ricci | |
| 2017/0136890 A1 | 5/2017 | Ricci | |
| 2017/0136891 A1 | 5/2017 | Ricci | |
| 2017/0136892 A1 | 5/2017 | Ricci | |
| 2017/0136893 A1 | 5/2017 | Ricci | |
| 2017/0136902 A1 | 5/2017 | Ricci | |
| 2017/0136903 A1 | 5/2017 | Ricci | |
| 2017/0136904 A1 | 5/2017 | Ricci | |
| 2017/0136905 A1 | 5/2017 | Ricci | |
| 2017/0136907 A1 | 5/2017 | Ricci | |
| 2017/0136910 A1 | 5/2017 | Ricci | |
| 2017/0136911 A1 | 5/2017 | Ricci | |
| 2017/0136912 A1 | 5/2017 | Ricci | |
| 2017/0140349 A1 | 5/2017 | Ricci | |
| 2017/0140603 A1 | 5/2017 | Ricci | |
| 2017/0274908 A1* | 9/2017 | Huai | G05D 1/0214 |
| 2017/0291608 A1* | 10/2017 | Engel | B60W 30/18163 |
| 2017/0334450 A1* | 11/2017 | Shiraishi | H04W 4/80 |
| 2017/0349184 A1* | 12/2017 | Tzirkel-Hancock | |
| | | | B60W 50/08 |
| 2017/0369052 A1* | 12/2017 | Nagy | B60W 50/08 |
| 2017/0369072 A1* | 12/2017 | Huber | B60W 50/0098 |
| 2017/0369073 A1* | 12/2017 | Huber | B60W 50/0098 |
| 2018/0113461 A1* | 4/2018 | Potnis | G05D 1/0088 |
| 2018/0129204 A1* | 5/2018 | Ricci | B60R 25/2018 |
| 2018/0136658 A1* | 5/2018 | Huai | G05D 1/0214 |
| 2018/0141562 A1* | 5/2018 | Singhal | B62D 15/00 |
| 2018/0144369 A1* | 5/2018 | Pouliot | B62D 15/00 |
| 2018/0208209 A1* | 7/2018 | Al-Dahle | B60W 50/0098 |
| 2019/0009788 A1* | 1/2019 | Phillips | G07C 5/0808 |
| 2019/0130664 A1* | 5/2019 | Appel | G07C 5/02 |

OTHER PUBLICATIONS

Davies, "This NIO EP9 performance EV wants to be the Tesla of supercars," Slashgear, 2016, https://www.slashgear.com/nextev-nio-ep9-car-tesla-of-performance-evs-21464829, 9 pages.

White, "NextEV's NIO EP9 is an incredible four-wheel-drive electric hypercar," Wired, 2016, retrieved from http://www.wired.co.uk/article/nextev-hypercar-nio-ep9, 6 pages.

"NIO ep9 Born to Push Limits," NIO, retrieved from https://web.archive.org/web/20161220175912/http://www.nio.io/ep9-experience, 6 pages.

* cited by examiner

METHOD AND SYSTEM FOR ADAPTIVE VEHICLE CONTROL IN AUTONOMOUS VEHICLES

CROSS REFERENCE TO RELATED APPLICATIONS

The present application claims the benefits of and priority, under 35 U.S.C. § 119(e), to U.S. Provisional Application Ser. No. 62/424,976, filed on Nov. 21, 2016, entitled "Next Generation Vehicle." The entire disclosure of the application listed above is hereby incorporated by reference, in its entirety, for all that it teaches and for all purposes.

FIELD

The present disclosure is generally directed to vehicle systems, in particular, toward electric and/or hybrid-electric vehicles.

BACKGROUND

In recent years, transportation methods have changed substantially. This change is due in part to a concern over the limited availability of natural resources, a proliferation in personal technology, and a societal shift to adopt more exterior environmentally friendly transportation solutions. These considerations have encouraged the development of a number of new flexible-fuel vehicles, hybrid-electric vehicles, and electric vehicles.

While these vehicles appear to be new they are generally implemented as a number of traditional subsystems that are merely tied to an alternative power source. In fact, the design and construction of the vehicles is limited to standard frame sizes, shapes, materials, and transportation concepts. Among other things, these limitations fail to take advantage of the benefits of new technology, power sources, and support infrastructure. In particular, the implementation of an artificially intelligent vehicle has lagged far behind the development vehicle subsystems.

DETAILED DESCRIPTION

Embodiments of the present disclosure will be described in connection with a vehicle, and in some embodiments, an electric vehicle, rechargeable electric vehicle, and/or hybrid-electric vehicle and associated systems.

Embodiments can provide an intelligent vehicle that controls autonomously vehicle driving operations using an operator-based, as opposed to a vehicle mode-based, profile that is selected by the operator. Operator and other object profiles can be stored locally or remotely in a cloud-based architecture and be portable to the operator regardless of the particular vehicle he or she operates. The portability of the profile further permits behavior of nearby objects to be predicted by providing a profile for the nearby object to the selected vehicle currently under autonomous control.

Figure 1:
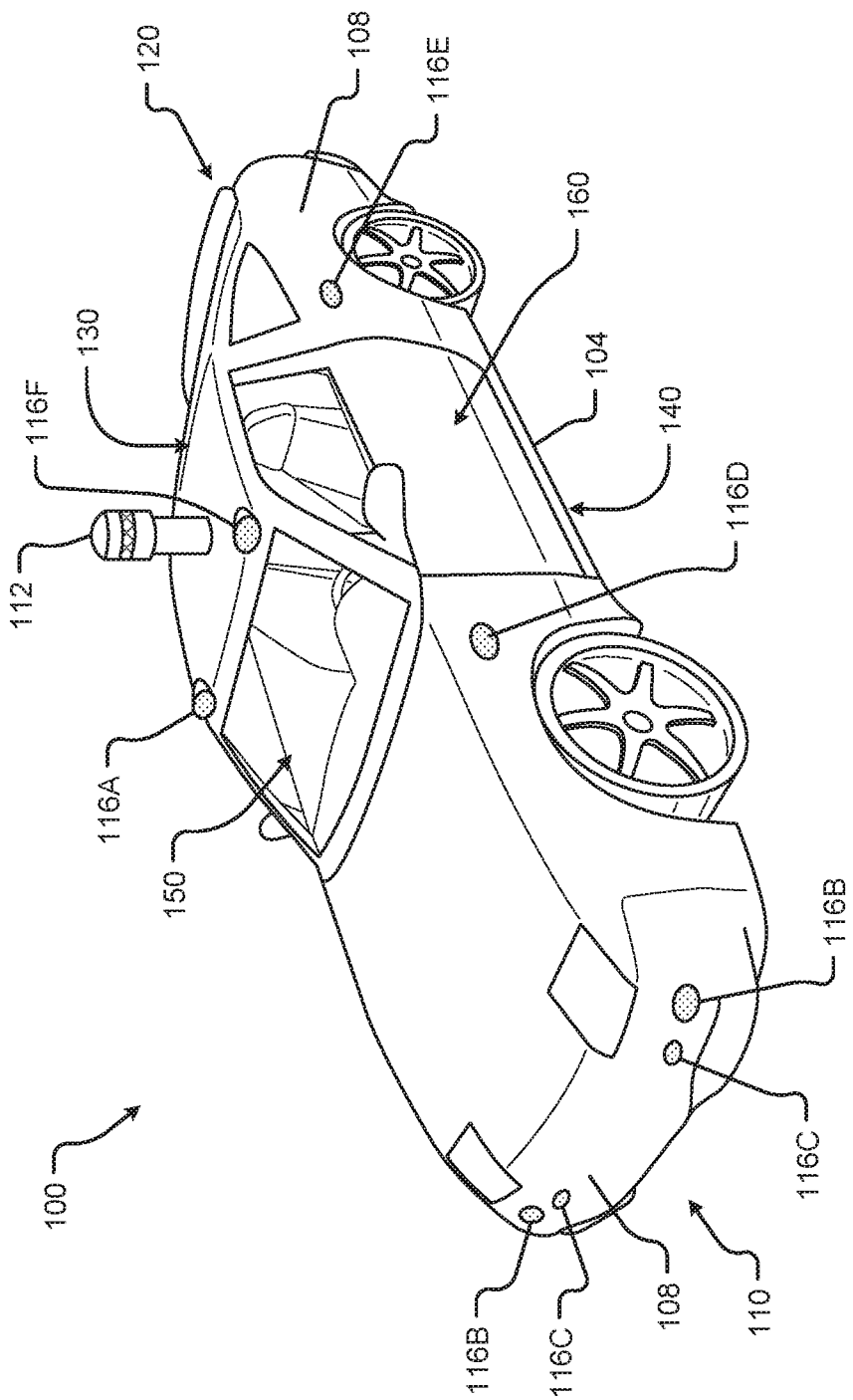
FIG. 1 shows a vehicle in accordance with embodiments of the present disclosure.

FIG. 1 shows a perspective view of a vehicle 100 in accordance with embodiments of the present disclosure. The electric vehicle 100 comprises a vehicle front 110, vehicle aft or rear 120, vehicle roof 130, at least one vehicle side 160, a vehicle undercarriage 140, and a vehicle interior 150. In any event, the vehicle 100 may include a frame 104 and one or more body panels 108 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components, etc.

Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like.

In some embodiments, the vehicle 100 may include a number of sensors, devices, and/or systems that are capable of assisting in driving operations. Examples of the various sensors and systems may include, but are in no way limited to, one or more of cameras (e.g., independent, stereo, combined image, etc.), infrared (IR) sensors, radio frequency (RF) sensors, ultrasonic sensors (e.g., transducers, transceivers, etc.), RADAR sensors (e.g., object-detection sensors and/or systems), LIDAR systems, odometry sensors and/or devices (e.g., encoders, etc.), orientation sensors (e.g., accelerometers, gyroscopes, magnetometer, etc.), navigation sensors and systems (e.g., GPS, etc.), and other ranging, imaging, and/or object-detecting sensors. The sensors may be disposed in an interior space 150 of the vehicle 100 and/or on an outside of the vehicle 100. In some embodiments, the sensors and systems may be disposed in one or more portions of a vehicle 100 (e.g., the frame 104, a body panel, a compartment, etc.).

The vehicle sensors and systems may be selected and/or configured to suit a level of operation associated with the vehicle 100. Among other things, the number of sensors used in a system may be altered to increase or decrease information available to a vehicle control system (e.g., affecting control capabilities of the vehicle 100). Additionally or alternatively, the sensors and systems may be part of one or more advanced driver assistance systems (ADAS) associated with a vehicle 100. In any event, the sensors and systems may be used to provide driving assistance at any level of operation (e.g., from fully-manual to fully-autonomous operations, etc.) as described herein.

The various levels of vehicle control and/or operation can be described as corresponding to a level of autonomy associated with a vehicle 100 for vehicle driving operations. For instance, at Level 0, or fully-manual driving operations, a driver (e.g., a human driver) may be responsible for all the driving control operations (e.g., steering, accelerating, braking, etc.) associated with the vehicle. Level 0 may be referred to as a "No Automation" level. At Level 1, the vehicle may be responsible for a limited number of the driving operations associated with the vehicle, while the driver is still responsible for most driving control operations. An example of a Level 1 vehicle may include a vehicle in which the throttle control and/or braking operations may be controlled by the vehicle (e.g., cruise control operations, etc.). Level 1 may be referred to as a "Driver Assistance" level. At Level 2, the vehicle may collect information (e.g., via one or more driving assistance systems, sensors, etc.) about an environment of the vehicle (e.g., surrounding area, roadway, traffic, ambient conditions, etc.) and use the collected information to control driving operations (e.g., steering, accelerating, braking, etc.) associated with the vehicle. In a Level 2 autonomous vehicle, the driver may be required to perform other aspects of driving operations not controlled by the vehicle. Level 2 may be referred to as a "Partial Automation" level. It should be appreciated that Levels 0-2 all involve the driver monitoring the driving operations of the vehicle.

At Level 3, the driver may be separated from controlling all the driving operations of the vehicle except when the vehicle makes a request for the operator to act or intervene in controlling one or more driving operations. In other words, the driver may be separated from controlling the vehicle unless the driver is required to take over for the vehicle. Level 3 may be referred to as a "Conditional Automation" level. At Level 4, the driver may be separated from controlling all the driving operations of the vehicle and the vehicle may control driving operations even when a user fails to respond to a request to intervene. Level 4 may be referred to as a "High Automation" level. At Level 5, the vehicle can control all the driving operations associated with the vehicle in all driving modes. The vehicle in Level 5 may continually monitor traffic, vehicular, roadway, and/or exterior environmental conditions while driving the vehicle. In Level 5, there is no human driver interaction required in any driving mode. Accordingly, Level 5 may be referred to as a "Full Automation" level. It should be appreciated that in Levels 3-5 the vehicle, and/or one or more automated driving systems associated with the vehicle, monitors the driving operations of the vehicle and the driving environment.

As shown in FIG. 1, the vehicle 100 may, for example, include at least one of a ranging and imaging system 112 (e.g., LIDAR, etc.), an imaging sensor 116A, 116F (e.g., camera, IR, etc.), a radio object-detection and ranging system sensors 116B (e.g., RADAR, RF, etc.), ultrasonic sensors 116C, and/or other object-detection sensors 116D, 116E. In some embodiments, the LIDAR system 112 and/or sensors may be mounted on a roof 130 of the vehicle 100. In one embodiment, the RADAR sensors 116B may be disposed at least at a front 110, aft 120, or side 160 of the vehicle 100. Among other things, the RADAR sensors may be used to monitor and/or detect a position of other vehicles, pedestrians, and/or other objects near, or proximal to, the vehicle 100. While shown associated with one or more areas of a vehicle 100, it should be appreciated that any of the sensors and systems 116A-K, 112 illustrated in FIGS. 1 and 2 may be disposed in, on, and/or about the vehicle 100 in any position, area, and/or zone of the vehicle 100.

Figure 2:
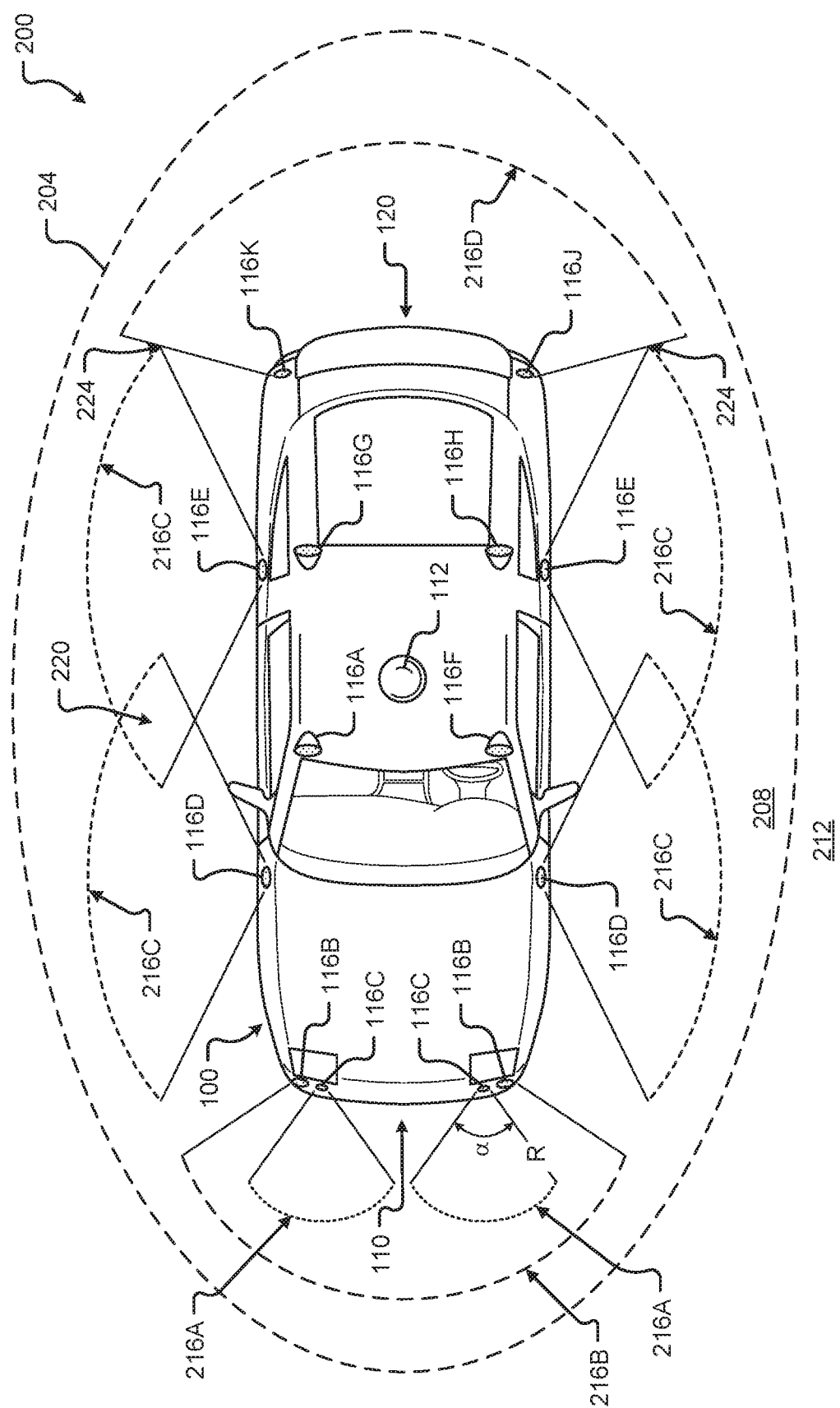
FIG. 2 shows a plan view of the vehicle in accordance with at least some embodiments of the present disclosure.

Referring now to FIG. 2, a plan view of a vehicle 100 will be described in accordance with embodiments of the present disclosure. In particular, FIG. 2 shows a vehicle sensing environment 200 at least partially defined by the sensors and systems 116A-K, 112 disposed in, on, and/or about the vehicle 100. Each sensor 116A-K may include an operational detection range R and operational detection angle $\alpha$. The operational detection range R may define the effective detection limit, or distance, of the sensor 116A-K. In some cases, this effective detection limit may be defined as a distance from a portion of the sensor 116A-K (e.g., a lens, sensing surface, etc.) to a point in space offset from the sensor 116A-K. The effective detection limit may define a distance, beyond which, the sensing capabilities of the sensor 116A-K deteriorate, fail to work, or are unreliable. In some embodiments, the effective detection limit may define a distance, within which, the sensing capabilities of the sensor 116A-K are able to provide accurate and/or reliable detection information. The operational detection angle $\alpha$ may define at least one angle of a span, or between horizontal and/or vertical limits, of a sensor 116A-K. As can be appreciated, the operational detection limit and the operational detection angle $\alpha$ of a sensor 116A-K together may define the effective detection zone 216A-D (e.g., the effective detection area, and/or volume, etc.) of a sensor 116A-K.

In some embodiments, the vehicle 100 may include a ranging and imaging system 112 such as LIDAR, or the like. The ranging and imaging system 112 may be configured to detect visual information in an environment surrounding the vehicle 100. The visual information detected in the environment surrounding the ranging and imaging system 112 may be processed (e.g., via one or more sensor and/or system processors, etc.) to generate a complete 360-degree view of an environment 200 around the vehicle. The ranging and imaging system 112 may be configured to generate changing 360-degree views of the environment 200 in real-time, for instance, as the vehicle 100 drives. In some cases, the ranging and imaging system 112 may have an effective detection limit 204 that is some distance from the center of the vehicle 100 outward over 360 degrees. The effective detection limit 204 of the ranging and imaging system 112 defines a view zone 208 (e.g., an area and/or volume, etc.) surrounding the vehicle 100. Any object falling outside of the view zone 208 is in the undetected zone 212 and would not be detected by the ranging and imaging system 112 of the vehicle 100.

Sensor data and information may be collected by one or more sensors or systems 116A-K, 112 of the vehicle 100 monitoring the vehicle sensing environment 200. This information may be processed (e.g., via a processor, computer-vision system, etc.) to determine targets (e.g., objects, signs, people, markings, roadways, conditions, etc.) inside one or more detection zones 208, 216A-D associated with the vehicle sensing environment 200. In some cases, information from multiple sensors 116A-K may be processed to form composite sensor detection information. For example, a first sensor 116A and a second sensor 116F may correspond to a first camera 116A and a second camera 116F aimed in a forward traveling direction of the vehicle 100. In this example, images collected by the cameras 116A, 116F may be combined to form stereo image information. This composite information may increase the capabilities of a single sensor in the one or more sensors 116A-K by, for example, adding the ability to determine depth associated with targets in the one or more detection zones 208, 216A-D. Similar image data may be collected by rear view cameras (e.g., sensors 116G, 116H) aimed in a rearward traveling direction vehicle 100.

In some embodiments, multiple sensors 116A-K may be effectively joined to increase a sensing zone and provide increased sensing coverage. For instance, multiple RADAR sensors 116B disposed on the front 110 of the vehicle may be joined to provide a zone 216B of coverage that spans across an entirety of the front 110 of the vehicle. In some cases, the multiple RADAR sensors 116B may cover a detection zone 216B that includes one or more other sensor detection zones 216A. These overlapping detection zones may provide redundant sensing, enhanced sensing, and/or provide greater detail in sensing within a particular portion (e.g., zone 216A) of a larger zone (e.g., zone 216B). Additionally or alternatively, the sensors 116A-K of the vehicle 100 may be arranged to create a complete coverage, via one or more sensing zones 208, 216A-D around the vehicle 100. In some areas, the sensing zones 216C of two or more sensors 116D, 116E may intersect at an overlap zone 220. In some areas, the angle and/or detection limit of two or more sensing zones 216C, 216D (e.g., of two or more sensors 116E, 116J, 116K) may meet at a virtual intersection point 224.

The vehicle 100 may include a number of sensors 116E, 116G, 116H, 116J, 116K disposed proximal to the rear 120 of the vehicle 100. These sensors can include, but are in no way limited to, an imaging sensor, camera, IR, a radio object-detection and ranging sensors, RADAR, RF, ultrasonic sensors, and/or other object-detection sensors. Among other things, these sensors 116E, 116G, 116H, 116J, 116K may detect targets near or approaching the rear of the vehicle 100. For example, another vehicle approaching the rear 120 of the vehicle 100 may be detected by one or more of the ranging and imaging system (e.g., LIDAR) 112, rear-view cameras 116G, 116H, and/or rear facing RADAR sensors 116J, 116K. As described above, the images from the rear-view cameras 116G, 116H may be processed to generate a stereo view (e.g., providing depth associated with an object or environment, etc.) for targets visible to both cameras 116G, 116H. As another example, the vehicle 100 may be driving and one or more of the ranging and imaging system 112, front-facing cameras 116A, 116F, front-facing RADAR sensors 116B, and/or ultrasonic sensors 116C may detect targets in front of the vehicle 100. This approach may provide critical sensor information to a vehicle control system in at least one of the autonomous driving levels described above. For instance, when the vehicle 100 is driving autonomously (e.g., Level 3, Level 4, or Level 5) and detects other vehicles stopped in a travel path, the sensor detection information may be sent to the vehicle control system of the vehicle 100 to control a driving operation (e.g., braking, decelerating, etc.) associated with the vehicle 100 (in this example, slowing the vehicle 100 as to avoid colliding with the stopped other vehicles). As yet another example, the vehicle 100 may be operating and one or more of the ranging and imaging system 112, and/or the side-facing sensors 116D, 116E (e.g., RADAR, ultrasonic, camera, combinations thereof, and/or other type of sensor), may detect targets at a side of the vehicle 100. It should be appreciated that the sensors 116A-K may detect a target that is both at a side 160 and a front 110 of the vehicle 100 (e.g., disposed at a diagonal angle to a centerline of the vehicle 100 running from the front 110 of the vehicle 100 to the rear 120 of the vehicle). Additionally or alternatively, the sensors 116A-K may detect a target that is both, or simultaneously, at a side 160 and a rear 120 of the vehicle 100 (e.g., disposed at a diagonal angle to the centerline of the vehicle 100).

Figure 3:
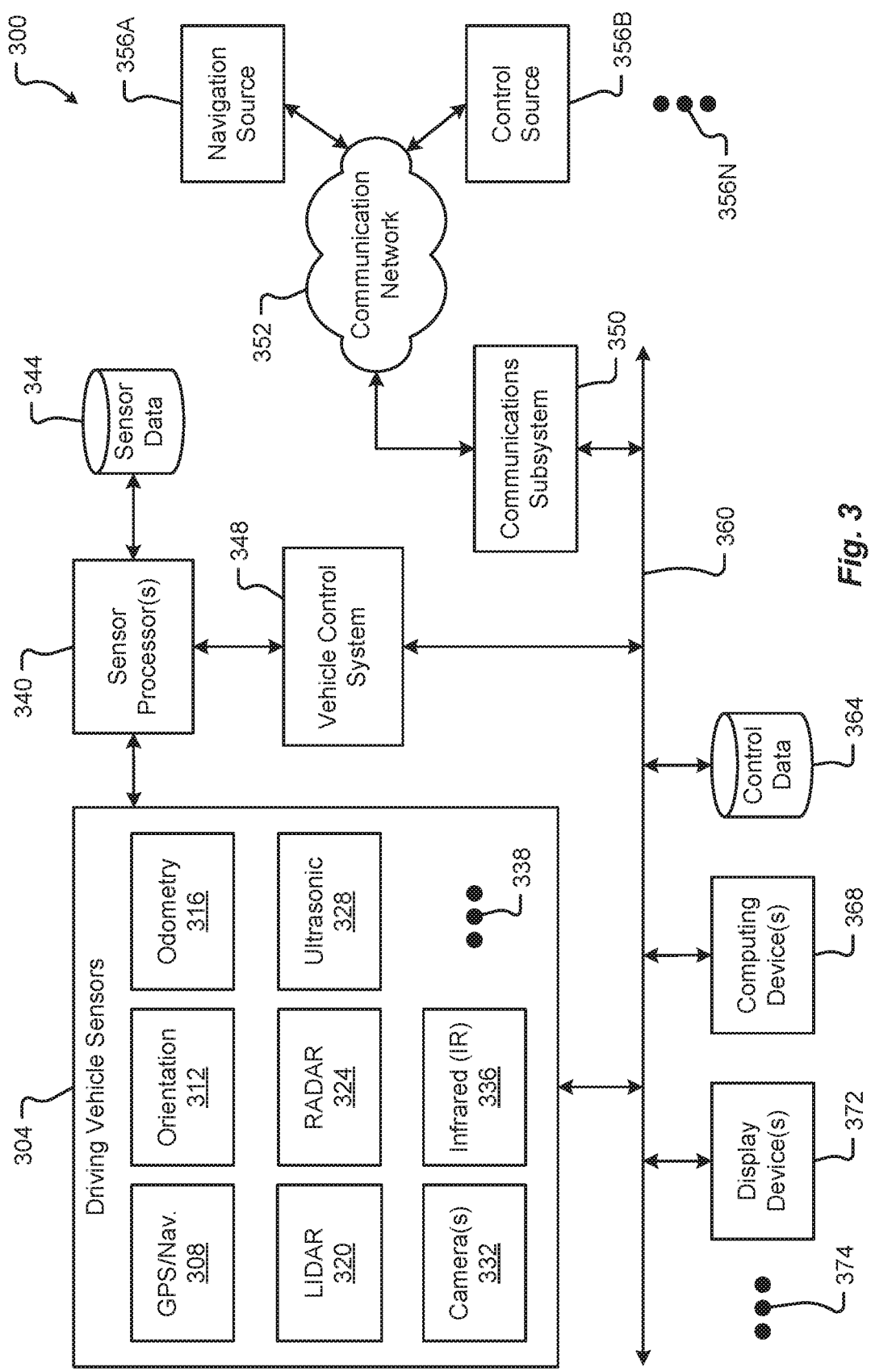
FIG. 3 is a block diagram of an embodiment of a communication environment of the vehicle in accordance with embodiments of the present disclosure.

FIG. 3 is a is a block diagram of an embodiment of a communication environment 300 of the vehicle 100 in accordance with embodiments of the present disclosure. The communication system 300 may include one or more vehicle driving vehicle sensors and systems 304, sensor processors 340, sensor data memory 344, vehicle control system 348, communications subsystem 350, control data 364, computing devices 368, display devices 372, and other components 374 that may be associated with a vehicle 100. These associated components may be electrically and/or communicatively coupled to one another via at least one bus 360. In some embodiments, the one or more associated components may send and/or receive signals across a communication network 352 to at least one of a navigation source 356A, a control source 356B, or some other entity 356N.

In accordance with at least some embodiments of the present disclosure, the communication network 352 may comprise any type of known communication medium or collection of communication media and may use any type of protocols, such as SIP, TCP/IP, SNA, IPX, AppleTalk, and the like, to transport messages between endpoints. The communication network 352 may include wired and/or wireless communication technologies. The Internet is an example of the communication network 352 that constitutes an Internet Protocol (IP) network consisting of many computers, computing networks, and other communication devices located all over the world, which are connected through many telephone systems and other means. Other examples of the communication network 104 include, without limitation, a standard Plain Old Telephone System (POTS), an Integrated Services Digital Network (ISDN), the Public Switched Telephone Network (PSTN), a Local Area Network (LAN), such as an Ethernet network, a Token-Ring network and/or the like, a Wide Area Network (WAN), a virtual network, including without limitation a virtual private network ("VPN"); the Internet, an intranet, an extranet, a cellular network, an infra-red network; a wireless network (e.g., a network operating under any of the IEEE 802.9 suite of protocols, the Bluetooth® protocol known in the art, and/or any other wireless protocol), and any other type of packet-switched or circuit-switched network known in the art and/or any combination of these and/or other networks. In addition, it can be appreciated that the communication network 352 need not be limited to any one network type, and instead may be comprised of a number of different networks and/or network types. The communication network 352 may comprise a number of different communication media such as coaxial cable, copper cable/wire, fiber-optic cable, antennas for transmitting/receiving wireless messages, and combinations thereof.

The driving vehicle sensors and systems 304 may include at least one navigation 308 (e.g., global positioning system (GPS), etc.), orientation 312, odometry 316, LIDAR 320, RADAR 324, ultrasonic 328, camera 332, infrared (IR) 336, and/or other sensor or system 338. These driving vehicle sensors and systems 304 may be similar, if not identical, to the sensors and systems 116A-K, 112 described in conjunction with FIGS. 1 and 2.

The navigation sensor 308 may include one or more sensors having receivers and antennas that are configured to utilize a satellite-based navigation system including a network of navigation satellites capable of providing geolocation and time information to at least one component of the vehicle 100. Examples of the navigation sensor 308 as described herein may include, but are not limited to, at least one of Garmin® GLO™ family of GPS and GLONASS combination sensors, Garmin® GPS 15x™ family of sensors, Garmin® GPS 16x™ family of sensors with high-sensitivity receiver and antenna, Garmin® GPS 18x OEM family of high-sensitivity GPS sensors, Dewetron DEWE-VGPS series of GPS sensors, GlobalSat 1-Hz series of GPS sensors, other industry-equivalent navigation sensors and/or systems, and may perform navigational and/or geolocation functions using any known or future-developed standard and/or architecture.

The orientation sensor 312 may include one or more sensors configured to determine an orientation of the vehicle 100 relative to at least one reference point. In some embodiments, the orientation sensor 312 may include at least one pressure transducer, stress/strain gauge, accelerometer, gyroscope, and/or geomagnetic sensor. Examples of the navigation sensor 308 as described herein may include, but are not limited to, at least one of Bosch Sensortec BMX 160 series low-power absolute orientation sensors, Bosch Sensortec BMX055 9-axis sensors, Bosch Sensortec BMI055 6-axis inertial sensors, Bosch Sensortec BMI160 6-axis inertial sensors, Bosch Sensortec BNIF055 9-axis inertial sensors (accelerometer, gyroscope, and magnetometer) with integrated Cortex MO+ microcontroller, Bosch Sensortec BMP280 absolute barometric pressure sensors, Infineon TLV493D-A1B6 3D magnetic sensors, Infineon TLI493D-W1B6 3D magnetic sensors, Infineon TL family of 3D magnetic sensors, Murata Electronics SCC2000 series combined gyro sensor and accelerometer, Murata Electronics SCC1300 series combined gyro sensor and accelerometer, other industry-equivalent orientation sensors and/or systems, and may perform orientation detection and/or determination functions using any known or future-developed standard and/or architecture.

The odometry sensor and/or system 316 may include one or more components that is configured to determine a change in position of the vehicle 100 over time. In some embodiments, the odometry system 316 may utilize data from one or more other sensors and/or systems 304 in determining a position (e.g., distance, location, etc.) of the vehicle 100 relative to a previously measured position for the vehicle 100. Additionally or alternatively, the odometry sensors 316 may include one or more encoders, Hall speed sensors, and/or other measurement sensors/devices configured to measure a wheel speed, rotation, and/or number of revolutions made over time. Examples of the odometry sensor/system 316 as described herein may include, but are not limited to, at least one of Infineon TLE4924/26/27/28C high-performance speed sensors, Infineon TL4941plusC(B) single chip differential Hall wheel-speed sensors, Infineon TL5041plusC Giant Mangnetoresistance (GMR) effect sensors, Infineon TL family of magnetic sensors, EPC Model 25SP Accu-CoderPro™ incremental shaft encoders, EPC Model 30M compact incremental encoders with advanced magnetic sensing and signal processing technology, EPC Model 925 absolute shaft encoders, EPC Model 958 absolute shaft encoders, EPC Model MA36S/MA63S/SA36S absolute shaft encoders, Dynapar™ F18 commutating optical encoder, Dynapar™ HS35R family of phased array encoder sensors, other industry-equivalent odometry sensors and/or systems, and may perform change in position detection and/or determination functions using any known or future-developed standard and/or architecture.

The LIDAR sensor/system 320 may include one or more components configured to measure distances to targets using laser illumination. In some embodiments, the LIDAR sensor/system 320 may provide 3D imaging data of an environment around the vehicle 100. The imaging data may be processed to generate a full 360-degree view of the environment around the vehicle 100. The LIDAR sensor/system 320 may include a laser light generator configured to generate a plurality of target illumination laser beams (e.g., laser light channels). In some embodiments, this plurality of laser beams may be aimed at, or directed to, a rotating reflective surface (e.g., a mirror) and guided outwardly from the LIDAR sensor/system 320 into a measurement environment. The rotating reflective surface may be configured to continually rotate 360 degrees about an axis, such that the plurality of laser beams is directed in a full 360-degree range around the vehicle 100. A photodiode receiver of the LIDAR sensor/system 320 may detect when light from the plurality of laser beams emitted into the measurement environment returns (e.g., reflected echo) to the LIDAR sensor/system 320. The LIDAR sensor/system 320 may calculate, based on a time associated with the emission of light to the detected return of light, a distance from the vehicle 100 to the illuminated target. In some embodiments, the LIDAR sensor/system 320 may generate over 2.0 million points per second and have an effective operational range of at least 100 meters. Examples of the LIDAR sensor/system 320 as described herein may include, but are not limited to, at least one of Velodyne® LiDAR™ HDL-64E 64-channel LIDAR sensors, Velodyne® LiDAR™ HDL-32E 32-channel LIDAR sensors, Velodyne® LiDAR™ PUCK™ VLP-16 16-channel LIDAR sensors, Leica Geosystems Pegasus: Two mobile sensor platform, Garmin® LIDAR-Lite v3 measurement sensor, Quanergy M8 LiDAR sensors, Quanergy S3 solid state LiDAR sensor, LeddarTech® LeddarVU compact solid state fixed-beam LIDAR sensors, other industry-equivalent LIDAR sensors and/or systems, and may perform illuminated target and/or obstacle detection in an environment around the vehicle 100 using any known or future-developed standard and/or architecture.

The RADAR sensors 324 may include one or more radio components that are configured to detect objects/targets in an environment of the vehicle 100. In some embodiments, the RADAR sensors 324 may determine a distance, position, and/or movement vector (e.g., angle, speed, etc.) associated with a target over time. The RADAR sensors 324 may include a transmitter configured to generate and emit electromagnetic waves (e.g., radio, microwaves, etc.) and a receiver configured to detect returned electromagnetic waves. In some embodiments, the RADAR sensors 324 may include at least one processor configured to interpret the returned electromagnetic waves and determine locational properties of targets. Examples of the RADAR sensors 324 as described herein may include, but are not limited to, at least one of Infineon RASIC™ RTN7735PL transmitter and RRN7745PL/46PL receiver sensors, Autoliv ASP Vehicle RADAR sensors, Delphi L2C0051TR 77 GHz ESR Electronically Scanning Radar sensors, Fujitsu Ten Ltd. Automotive Compact 77 GHz 3D Electronic Scan Millimeter Wave Radar sensors, other industry-equivalent RADAR sensors and/or systems, and may perform radio target and/or obstacle detection in an environment around the vehicle 100 using any known or future-developed standard and/or architecture.

The ultrasonic sensors 328 may include one or more components that are configured to detect objects/targets in an environment of the vehicle 100. In some embodiments, the ultrasonic sensors 328 may determine a distance, position, and/or movement vector (e.g., angle, speed, etc.) associated with a target over time. The ultrasonic sensors 328 may include an ultrasonic transmitter and receiver, or transceiver, configured to generate and emit ultrasound waves and interpret returned echoes of those waves. In some embodiments, the ultrasonic sensors 328 may include at least one processor configured to interpret the returned ultrasonic waves and determine locational properties of targets. Examples of the ultrasonic sensors 328 as described herein may include, but are not limited to, at least one of Texas Instruments TIDA-00151 automotive ultrasonic sensor interface IC sensors, MaxBotix® MB8450 ultrasonic proximity sensor, MaxBotix® ParkSonar™-EZ ultrasonic proximity sensors, Murata Electronics MA40H1S-R open-structure ultrasonic sensors, Murata Electronics MA40S4R/S open-structure ultrasonic sensors, Murata Electronics MA58MF14-7N waterproof ultrasonic sensors, other industry-equivalent ultrasonic sensors and/or systems, and may perform ultrasonic target and/or obstacle detection in an environment around the vehicle 100 using any known or future-developed standard and/or architecture.

The camera sensors 332 may include one or more components configured to detect image information associated with an environment of the vehicle 100. In some embodiments, the camera sensors 332 may include a lens, filter, image sensor, and/or a digital image processer. It is an aspect of the present disclosure that multiple camera sensors 332 may be used together to generate stereo images providing depth measurements. Examples of the camera sensors 332 as described herein may include, but are not limited to, at least one of ON Semiconductor® MT9V024 Global Shutter VGA GS CMOS image sensors, Teledyne DALSA Falcon2 camera sensors, CMOSIS CMV50000 high-speed CMOS image sensors, other industry-equivalent camera sensors and/or systems, and may perform visual target and/or obstacle detection in an environment around the vehicle 100 using any known or future-developed standard and/or architecture.

The infrared (IR) sensors 336 may include one or more components configured to detect image information associated with an environment of the vehicle 100. The IR sensors 336 may be configured to detect targets in low-light, dark, or poorly-lit environments. The IR sensors 336 may include an IR light emitting element (e.g., IR light emitting diode (LED), etc.) and an IR photodiode. In some embodiments, the IR photodiode may be configured to detect returned IR light at or about the same wavelength to that emitted by the IR light emitting element. In some embodiments, the IR sensors 336 may include at least one processor configured to interpret the returned IR light and determine locational properties of targets. The IR sensors 336 may be configured to detect and/or measure a temperature associated with a target (e.g., an object, pedestrian, other vehicle, etc.). Examples of IR sensors 336 as described herein may include, but are not limited to, at least one of Opto Diode lead-salt IR array sensors, Opto Diode OD-850 Near-IR LED sensors, Opto Diode SA/SHA727 steady state IR emitters and IR detectors, FLIR® LS microbolometer sensors, FLIR® TacFLIR 380-HD InSb MWIR FPA and HD MWIR thermal sensors, FLIR® VOx 640×480 pixel detector sensors, Delphi IR sensors, other industry-equivalent IR sensors and/or systems, and may perform IR visual target and/or obstacle detection in an environment around the vehicle 100 using any known or future-developed standard and/or architecture.

In some embodiments, the driving vehicle sensors and systems 304 may include other sensors 338 and/or combinations of the sensors 308-336 described above. Additionally or alternatively, one or more of the sensors 308-336 described above may include one or more processors configured to process and/or interpret signals detected by the one or more sensors 308-336. In some embodiments, the processing of at least some sensor information provided by the vehicle sensors and systems 304 may be processed by at least one sensor processor 340. Raw and/or processed sensor data may be stored in a sensor data memory 344 storage medium. In some embodiments, the sensor data memory 344 may store instructions used by the sensor processor 340 for processing sensor information provided by the sensors and systems 304. In any event, the sensor data memory 344 may be a disk drive, optical storage device, solid-state storage device such as a random access memory ("RAM") and/or a read-only memory ("ROM"), which can be programmable, flash-updateable, and/or the like.

The vehicle control system 348 may receive processed sensor information from the sensor processor 340 and determine to control an aspect of the vehicle 100. Controlling an aspect of the vehicle 100 may include presenting information via one or more display devices 372 associated with the vehicle, sending commands to one or more computing devices 368 associated with the vehicle, and/or controlling a driving operation of the vehicle. In some embodiments, the vehicle control system 348 may correspond to one or more computing systems that control driving operations of the vehicle 100 in accordance with the Levels of driving autonomy described above. In one embodiment, the vehicle control system 348 may operate a speed of the vehicle 100 by controlling an output signal to the accelerator and/or braking system of the vehicle. In this example, the vehicle control system 348 may receive sensor data describing an environment surrounding the vehicle 100 and, based on the sensor data received, determine to adjust the acceleration, power output, and/or braking of the vehicle 100. The vehicle control system 348 may additionally control steering and/or other driving functions of the vehicle 100.

The vehicle control system 348 may communicate, in real-time, with the driving sensors and systems 304 forming a feedback loop. In particular, upon receiving sensor information describing a condition of targets in the environment surrounding the vehicle 100, the vehicle control system 348 may autonomously make changes to a driving operation of the vehicle 100. The vehicle control system 348 may then receive subsequent sensor information describing any change to the condition of the targets detected in the environment as a result of the changes made to the driving operation. This continual cycle of observation (e.g., via the sensors, etc.) and action (e.g., selected control or non-control of vehicle operations, etc.) allows the vehicle 100 to operate autonomously in the environment.

In some embodiments, the one or more components of the vehicle 100 (e.g., the driving vehicle sensors 304, vehicle control system 348, display devices 372, etc.) may communicate across the communication network 352 to one or more entities 356A-N via a communications subsystem 350 of the vehicle 100. Embodiments of the communications subsystem 350 are described in greater detail in conjunction with FIG. 5. For instance, the navigation sensors 308 may receive global positioning, location, and/or navigational information from a navigation source 356A. In some embodiments, the navigation source 356A may be a global navigation satellite system (GNSS) similar, if not identical, to NAVSTAR GPS, GLONASS, EU Galileo, and/or the BeiDou Navigation Satellite System (BDS) to name a few.

In some embodiments, the vehicle control system 348 may receive control information from one or more control sources 356B. The control source 356 may provide vehicle control information including autonomous driving control commands, vehicle operation override control commands, and the like. The control source 356 may correspond to an autonomous vehicle control system, a traffic control system, an administrative control entity, and/or some other controlling server. It is an aspect of the present disclosure that the vehicle control system 348 and/or other components of the vehicle 100 may exchange communications with the control source 356 across the communication network 352 and via the communications subsystem 350.

Information associated with controlling driving operations of the vehicle 100 may be stored in a control data memory 364 storage medium. The control data memory 364 may store instructions used by the vehicle control system 348 for controlling driving operations of the vehicle 100, historical control information, autonomous driving control rules, and the like. In some embodiments, the control data memory 364 may be a disk drive, optical storage device, solid-state storage device such as a random access memory ("RAM") and/or a read-only memory ("ROM"), which can be programmable, flash-updateable, and/or the like.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 4:
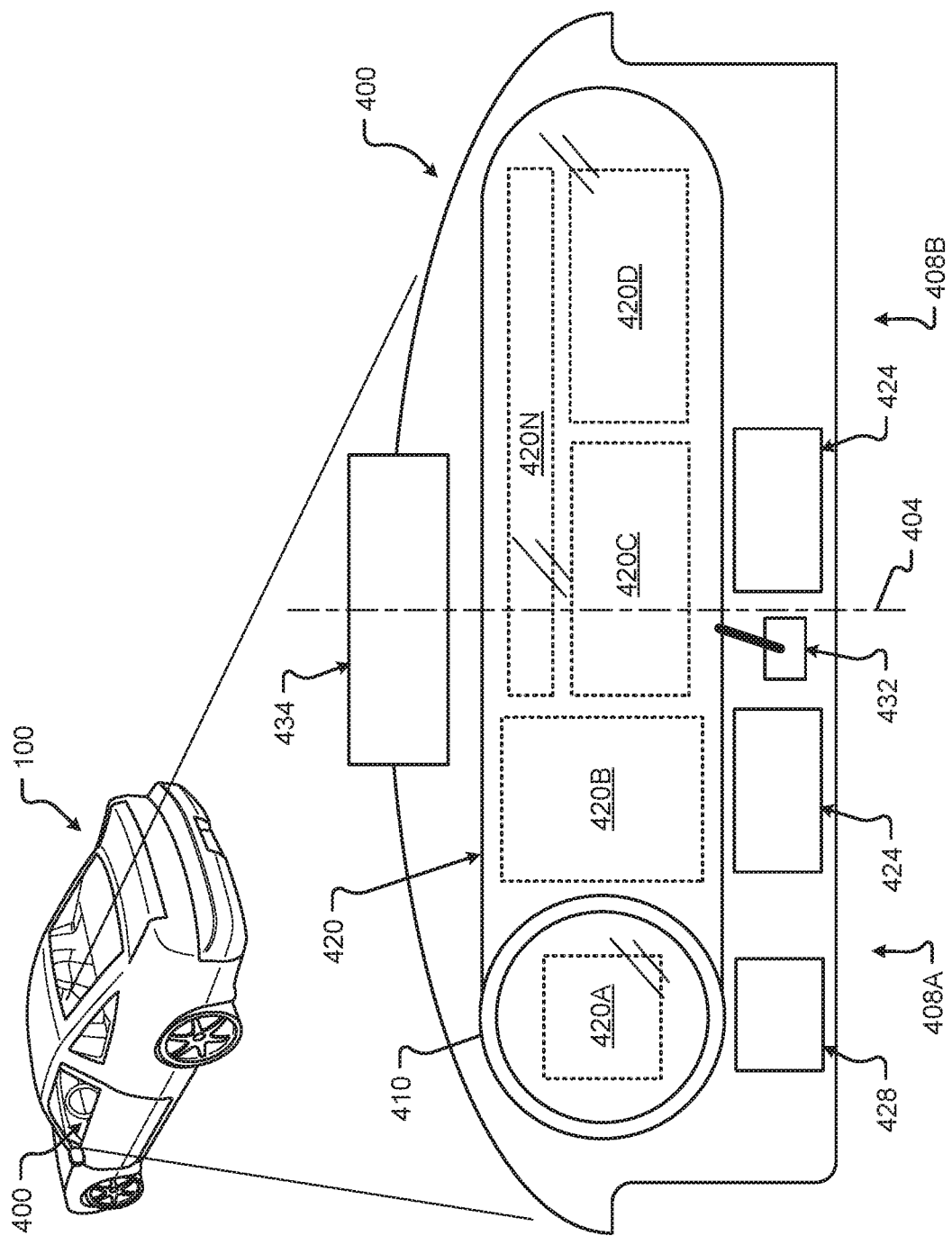
FIG. 4 shows an embodiment of the instrument panel of the vehicle according to one embodiment of the present disclosure.

FIG. 4 shows one embodiment of the instrument panel 400 of the vehicle 100. The instrument panel 400 of vehicle 100 comprises a steering wheel 410, a vehicle operational display 420 (e.g., configured to present and/or display driving data such as speed, measured air resistance, vehicle information, entertainment information, etc.), one or more auxiliary displays 424 (e.g., configured to present and/or display information segregated from the operational display 420, entertainment applications, movies, music, etc.), a heads-up display 434 (e.g., configured to display any information previously described including, but in no way limited to, guidance information such as route to destination, or obstacle warning information to warn of a potential collision, or some or all primary vehicle operational data such as speed, resistance, etc.), a power management display 428 (e.g., configured to display data corresponding to electric power levels of vehicle 100, reserve power, charging status, etc.), and an input device 432 (e.g., a controller, touchscreen, or other interface device configured to interface with one or more displays in the instrument panel or components of the vehicle 100. The input device 432 may be configured as a joystick, mouse, touchpad, tablet, 3D gesture capture device, etc.). In some embodiments, the input device 432 may be used to manually maneuver a portion of the vehicle 100 into a charging position (e.g., moving a charging plate to a desired separation distance, etc.).

While one or more of displays of instrument panel 400 may be touch-screen displays, it should be appreciated that the vehicle operational display may be a display incapable of receiving touch input. For instance, the operational display 420 that spans across an interior space centerline 404 and across both a first zone 408A and a second zone 408B may be isolated from receiving input from touch, especially from a passenger. In some cases, a display that provides vehicle operation or critical systems information and interface may be restricted from receiving touch input and/or be configured as a non-touch display. This type of configuration can prevent dangerous mistakes in providing touch input where such input may cause an accident or unwanted control.

In some embodiments, one or more displays of the instrument panel 400 may be mobile devices and/or applications residing on a mobile device such as a smart phone. Additionally or alternatively, any of the information described herein may be presented to one or more portions 420A-N of the operational display 420 or other display 424, 428, 434. In one embodiment, one or more displays of the instrument panel 400 may be physically separated or detached from the instrument panel 400. In some cases, a detachable display may remain tethered to the instrument panel.

The portions 420A-N of the operational display 420 may be dynamically reconfigured and/or resized to suit any display of information as described. Additionally or alternatively, the number of portions 420A-N used to visually present information via the operational display 420 may be dynamically increased or decreased as required, and are not limited to the configurations shown.

Figure 5:
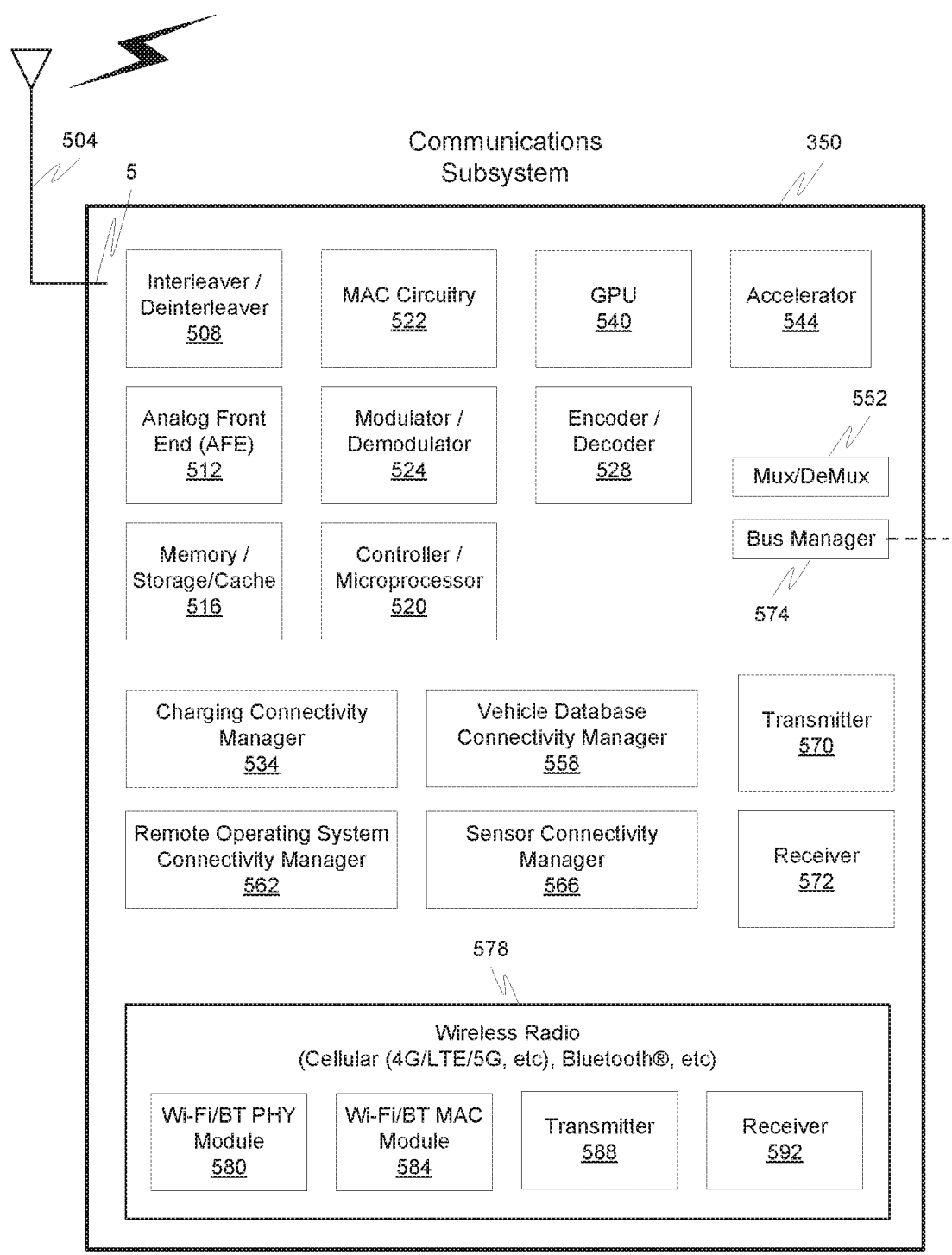
FIG. 5 is a block diagram of an embodiment of a communications subsystem of the vehicle.

FIG. 5 illustrates a hardware diagram of communications componentry that can be optionally associated with the vehicle 100 in accordance with embodiments of the present disclosure.

The communications componentry can include one or more wired or wireless devices such as a transceiver(s) and/or modem that allows communications not only between the various systems disclosed herein but also with other devices, such as devices on a network, and/or on a distributed network such as the Internet and/or in the cloud and/or with other vehicle(s).

The communications subsystem 350 can also include inter- and intra-vehicle communications capabilities such as hotspot and/or access point connectivity for any one or more of the vehicle occupants and/or vehicle-to-vehicle communications.

Additionally, and while not specifically illustrated, the communications subsystem 350 can include one or more communications links (that can be wired or wireless) and/or communications busses (managed by the bus manager 574), including one or more of CANbus, OBD-II, ARCINC 429, Byteflight, CAN (Controller Area Network), D2B (Domestic Digital Bus), FlexRay, DC-BUS, IDB-1394, IEBus, I2C, ISO 9141-1/-2, J1708, J1587, J1850, J1939, ISO 11783, Keyword Protocol 2000, LIN (Local Interconnect Network), MOST (Media Oriented Systems Transport), Multifunction Vehicle Bus, SMARTwireX, SPI, VAN (Vehicle Area Network), and the like or in general any communications protocol and/or standard(s).

The various protocols and communications can be communicated one or more of wirelessly and/or over transmission media such as single wire, twisted pair, fiber optic, IEEE 1394, MIL-STD-1553, MIL-STD-1773, power-line communication, or the like. (All of the above standards and protocols are incorporated herein by reference in their entirety).

As discussed, the communications subsystem 350 enables communications between any if the inter-vehicle systems and subsystems as well as communications with non-collocated resources, such as those reachable over a network such as the Internet.

The communications subsystem 350, in addition to well-known componentry (which has been omitted for clarity), includes interconnected elements including one or more of: one or more antennas 504, an interleaver/deinterleaver 508, an analog front end (AFE) 512, memory/storage/cache 516, controller/microprocessor 520, MAC circuitry 522, modulator/demodulator 524, encoder/decoder 528, a plurality of connectivity managers 534, 558, 562, 566, GPU 540, accelerator 544, a multiplexer/demultiplexer 552, transmitter 570, receiver 572 and wireless radio 578 components such as a Wi-Fi PHY/Bluetooth® module 580, a Wi-Fi/BT MAC module 584, transmitter 588 and receiver 592. The various elements in the device 350 are connected by one or more links/busses 5 (not shown, again for sake of clarity).

The device 350 can have one more antennas 504, for use in wireless communications such as multi-input multi-output (MIMO) communications, multi-user multi-input multi-output (MU-MIMO) communications Bluetooth®, LTE, 4G, 5G, Near-Field Communication (NFC), etc., and in general for any type of wireless communications. The antenna(s) 504 can include, but are not limited to one or more of directional antennas, omnidirectional antennas, monopoles, patch antennas, loop antennas, microstrip antennas, dipoles, and any other antenna(s) suitable for communication transmission/reception. In an exemplary embodiment, transmission/reception using MIMO may require particular antenna spacing. In another exemplary embodiment, MIMO transmission/reception can enable spatial diversity allowing for different channel characteristics at each of the antennas. In yet another embodiment, MIMO transmission/reception can be used to distribute resources to multiple users for example within the vehicle 100 and/or in another vehicle.

Antenna(s) 504 generally interact with the Analog Front End (AFE) 512, which is needed to enable the correct processing of the received modulated signal and signal conditioning for a transmitted signal. The AFE 512 can be functionally located between the antenna and a digital baseband system in order to convert the analog signal into a digital signal for processing and vice-versa.

The subsystem 350 can also include a controller/microprocessor 520 and a memory/storage/cache 516. The subsystem 350 can interact with the memory/storage/cache 516 which may store information and operations necessary for configuring and transmitting or receiving the information described herein. The memory/storage/cache 516 may also be used in connection with the execution of application programming or instructions by the controller/microprocessor 520, and for temporary or long term storage of program instructions and/or data. As examples, the memory/storage/cache 520 may comprise a computer-readable device, RAM, ROM, DRAM, SDRAM, and/or other storage device(s) and media.

The controller/microprocessor 520 may comprise a general purpose programmable processor or controller for executing application programming or instructions related to the subsystem 350. Furthermore, the controller/microprocessor 520 can perform operations for configuring and transmitting/receiving information as described herein. The controller/microprocessor 520 may include multiple processor cores, and/or implement multiple virtual processors. Optionally, the controller/microprocessor 520 may include multiple physical processors. By way of example, the controller/microprocessor 520 may comprise a specially configured Application Specific Integrated Circuit (ASIC) or other integrated circuit, a digital signal processor(s), a controller, a hardwired electronic or logic circuit, a programmable logic device or gate array, a special purpose computer, or the like.

The subsystem 350 can further include a transmitter 570 and receiver 572 which can transmit and receive signals, respectively, to and from other devices, subsystems and/or other destinations using the one or more antennas 504 and/or links/busses. Included in the subsystem 350 circuitry is the medium access control or MAC Circuitry 522. MAC circuitry 522 provides for controlling access to the wireless medium. In an exemplary embodiment, the MAC circuitry 522 may be arranged to contend for the wireless medium and configure frames or packets for communicating over the wired/wireless medium.

The subsystem 350 can also optionally contain a security module (not shown). This security module can contain information regarding but not limited to, security parameters required to connect the device to one or more other devices or other available network(s), and can include WEP or WPA/WPA-2 (optionally+AES and/or TKIP) security access keys, network keys, etc. The WEP security access key is a security password used by Wi-Fi networks. Knowledge of this code can enable a wireless device to exchange information with an access point and/or another device. The information exchange can occur through encoded messages with the WEP access code often being chosen by the network administrator. WPA is an added security standard that is also used in conjunction with network connectivity with stronger encryption than WEP.

In some embodiments, the communications subsystem 350 also includes a GPU 540, an accelerator 544, a Wi-Fi/BT/BLE PHY module 580 and a Wi-Fi/BT/BLE MAC module 584 and wireless transmitter 588 and receiver 592. In some embodiments, the GPU 540 may be a graphics processing unit, or visual processing unit, comprising at least one circuit and/or chip that manipulates and changes memory to accelerate the creation of images in a frame buffer for output to at least one display device. The GPU 540 may include one or more of a display device connection port, printed circuit board (PCB), a GPU chip, a metal-oxide-semiconductor field-effect transistor (MOSFET), memory (e.g., single data rate random-access memory (SDRAM), double data rate random-access memory (DDR) RAM, etc., and/or combinations thereof), a secondary processing chip (e.g., handling video out capabilities, processing, and/or other functions in addition to the GPU chip, etc.), a capacitor, heatsink, temperature control or cooling fan, motherboard connection, shielding, and the like.

The various connectivity managers 534, 558, 562, 566 manage and/or coordinate communications between the subsystem 350 and one or more of the systems disclosed herein and one or more other devices/systems. The connectivity managers 534, 558, 562, 566 include a charging connectivity manager 534, a vehicle database connectivity manager 558, a remote operating system connectivity manager 562, and a sensor connectivity manager 566.

The charging connectivity manager 534 can coordinate not only the physical connectivity between the vehicle 100 and a charging device/vehicle, but can also communicate with one or more of a power management controller, one or more third parties and optionally a billing system(s). As an example, the vehicle 100 can establish communications with the charging device/vehicle to one or more of coordinate interconnectivity between the two (e.g., by spatially aligning the charging receptacle on the vehicle with the charger on the charging vehicle) and optionally share navigation information. Once charging is complete, the amount of charge provided can be tracked and optionally forwarded to, for example, a third party for billing. In addition to being able to manage connectivity for the exchange of power, the charging connectivity manager 534 can also communicate information, such as billing information to the charging vehicle and/or a third party. This billing information could be, for example, the owner of the vehicle, the driver/occupant(s) of the vehicle, company information, or in general any information usable to charge the appropriate entity for the power received.

The vehicle database connectivity manager 558 allows the subsystem to receive and/or share information stored in the vehicle database. This information can be shared with other vehicle components/subsystems and/or other entities, such as third parties and/or charging systems. The information can also be shared with one or more vehicle occupant devices, such as an app (application) on a mobile device the driver uses to track information about the vehicle 100 and/or a dealer or service/maintenance provider. In general any information stored in the vehicle database can optionally be shared with any one or more other devices optionally subject to any privacy or confidentially restrictions.

The remote operating system connectivity manager 562 facilitates communications between the vehicle 100 and any one or more autonomous vehicle systems. These communications can include one or more of navigation information, vehicle information, other vehicle information, weather information, occupant information, or in general any information related to the remote operation of the vehicle 100.

The sensor connectivity manager 566 facilitates communications between any one or more of the vehicle sensors (e.g., the driving vehicle sensors and systems 304, etc.) and any one or more of the other vehicle systems. The sensor connectivity manager 566 can also facilitate communications between any one or more of the sensors and/or vehicle systems and any other destination, such as a service company, app, or in general to any destination where sensor data is needed.

In accordance with one exemplary embodiment, any of the communications discussed herein can be communicated via the conductor(s) used for charging. One exemplary protocol usable for these communications is Power-line communication (PLC). PLC is a communication protocol that uses electrical wiring to simultaneously carry both data, and Alternating Current (AC) electric power transmission or electric power distribution. It is also known as power-line carrier, power-line digital subscriber line (PDSL), mains communication, power-line telecommunications, or power-line networking (PLN). For DC environments in vehicles PLC can be used in conjunction with CAN-bus, LIN-bus over power line (DC-LIN) and DC-BUS.

The communications subsystem can also optionally manage one or more identifiers, such as an IP (internet protocol) address(es), associated with the vehicle and one or other system or subsystems or components therein. These identifiers can be used in conjunction with any one or more of the connectivity managers as discussed herein.

Figure 6:
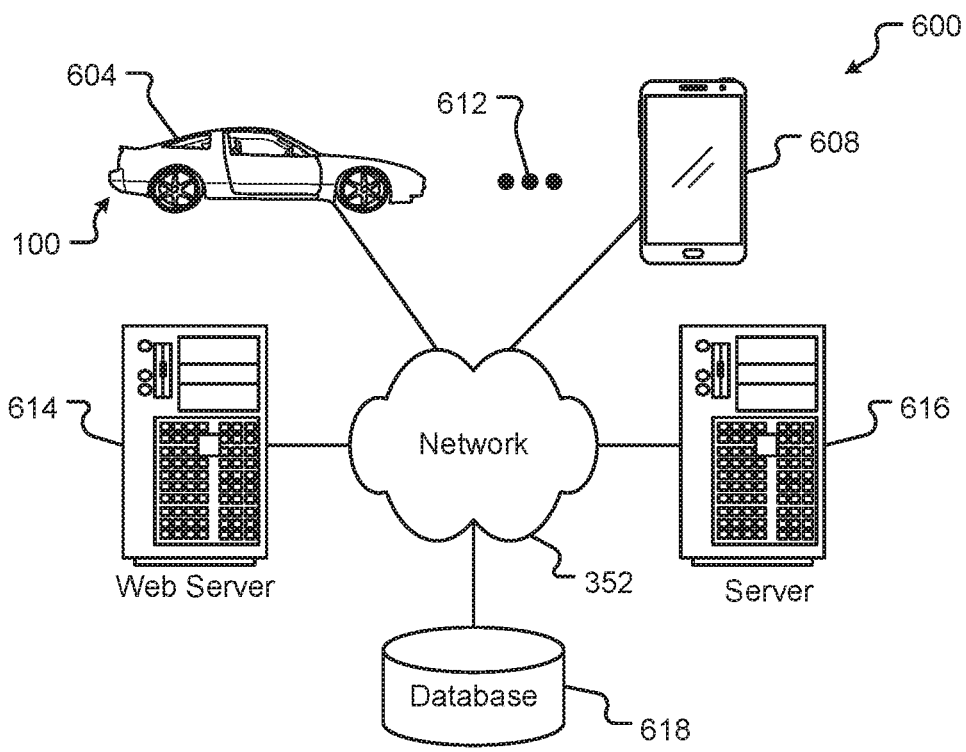
FIG. 6 is a block diagram of a computing environment associated with the embodiments presented herein.

FIG. 6 illustrates a block diagram of a computing environment 600 that may function as the servers, user computers, or other systems provided and described herein. The computing environment 600 includes one or more user computers, or computing devices, such as a vehicle computing device 604, a communication device 608, and/or more 612. The computing devices 604, 608, 612 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 604, 608, 612 may also have any of a variety of applications, including for example, database client and/or server applications, and web browser applications. Alternatively, the computing devices 604, 608, 612 may be any other electronic device, such as a thin-client computer, Internet-enabled mobile telephone, and/or personal digital assistant, capable of communicating via a network 352 and/or displaying and navigating web pages or other types of electronic documents. Although the exemplary computing environment 600 is shown with two computing devices, any number of user computers or computing devices may be supported.

The computing environment 600 may also include one or more servers 614, 616. In this example, server 614 is shown as a web server and server 616 is shown as an application server. The web server 614, which may be used to process requests for web pages or other electronic documents from computing devices 604, 608, 612. The web server 614 can be running an operating system including any of those discussed above, as well as any commercially-available server operating systems. The web server 614 can also run a variety of server applications, including SIP (Session Initiation Protocol) servers, HTTP(s) servers, FTP servers, CGI servers, database servers, Java servers, and the like. In some instances, the web server 614 may publish operations available operations as one or more web services.

The computing environment 600 may also include one or more file and or/application servers 616, which can, in addition to an operating system, include one or more applications accessible by a client running on one or more of the computing devices 604, 608, 612. The server(s) 616 and/or 614 may be one or more general purpose computers capable of executing programs or scripts in response to the computing devices 604, 608, 612. As one example, the server 616, 614 may execute one or more web applications. The web application may be implemented as one or more scripts or programs written in any programming language, such as Java™, C, C #®, or C++, and/or any scripting language, such as Perl, Python, or TCL, as well as combinations of any programming/scripting languages. The application server(s) 616 may also include database servers, including without limitation those commercially available from Oracle®, Microsoft®, Sybase®, IBM® and the like, which can process requests from database clients running on a computing device 604, 608, 612.

The web pages created by the server 614 and/or 616 may be forwarded to a computing device 604, 608, 612 via a web (file) server 614, 616. Similarly, the web server 614 may be able to receive web page requests, web services invocations, and/or input data from a computing device 604, 608, 612 (e.g., a user computer, etc.) and can forward the web page requests and/or input data to the web (application) server

616. In further embodiments, the server 616 may function as a file server. Although for ease of description, FIG. 6 illustrates a separate web server 614 and file/application server 616, those skilled in the art will recognize that the functions described with respect to servers 614, 616 may be performed by a single server and/or a plurality of specialized servers, depending on implementation-specific needs and parameters. The computer systems 604, 608, 612, web (file) server 614 and/or web (application) server 616 may function as the system, devices, or components described in FIGS. 1-6.

The computing environment 600 may also include a database 618. The database 618 may reside in a variety of locations. By way of example, database 618 may reside on a storage medium local to (and/or resident in) one or more of the computers 604, 608, 612, 614, 616. Alternatively, it may be remote from any or all of the computers 604, 608, 612, 614, 616, and in communication (e.g., via the network 610) with one or more of these. The database 618 may reside in a storage-area network ("SAN") familiar to those skilled in the art. Similarly, any necessary files for performing the functions attributed to the computers 604, 608, 612, 614, 616 may be stored locally on the respective computer and/or remotely, as appropriate. The database 618 may be a relational database, such as Oracle 20i®, that is adapted to store, update, and retrieve data in response to SQL-formatted commands.

Figure 7:
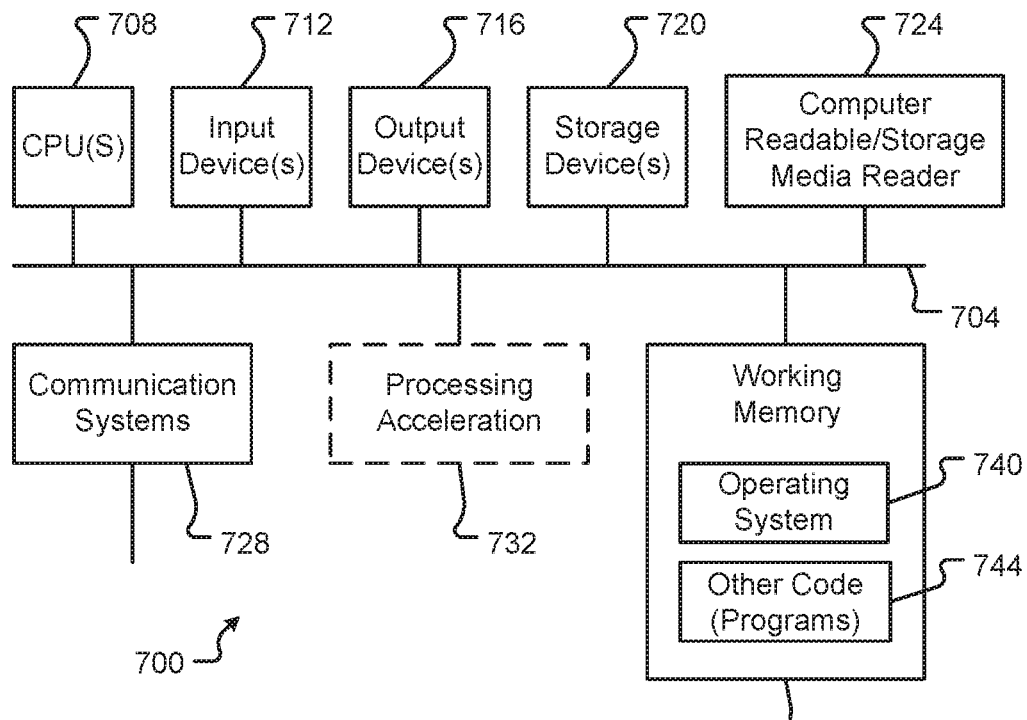
FIG. 7 is a block diagram of a computing device associated with one or more components described herein.

FIG. 7 illustrates one embodiment of a computer system 700 upon which the servers, user computers, computing devices, or other systems or components described above may be deployed or executed. The computer system 700 is shown comprising hardware elements that may be electrically coupled via a bus 704. The hardware elements may include one or more central processing units (CPUs) 708; one or more input devices 712 (e.g., a mouse, a keyboard, etc.); and one or more output devices 716 (e.g., a display device, a printer, etc.). The computer system 700 may also include one or more storage devices 720. By way of example, storage device(s) 720 may be disk drives, optical storage devices, solid-state storage devices such as a random access memory ("RAM") and/or a read-only memory ("ROM"), which can be programmable, flash-updateable and/or the like.

The computer system 700 may additionally include a computer-readable storage media reader 724; a communications system 728 (e.g., a modem, a network card (wireless or wired), an infra-red communication device, etc.); and working memory 736, which may include RAM and ROM devices as described above. The computer system 700 may also include a processing acceleration unit 732, which can include a DSP, a special-purpose processor, and/or the like.

The computer-readable storage media reader 724 can further be connected to a computer-readable storage medium, together (and, optionally, in combination with storage device(s) 720) comprehensively representing remote, local, fixed, and/or removable storage devices plus storage media for temporarily and/or more permanently containing computer-readable information. The communications system 728 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 700 may also comprise software elements, shown as being currently located within a working memory 736, including an operating system 740 and/or other code 744. It should be appreciated that alternate embodiments of a computer system 700 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 340, 708 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

As set forth below, the computer system 700, during vehicle operation, can capture and store operator and occupant information to working memory 736 and/or storage device(s) 720 and/or a remotely located profile database. The captured and stored information can include vehicle (control) parameters (e.g., steering angle, acceleration, deceleration, inter-vehicle distance, and the like) in response to sensed objects on the road (e.g., sensed object information), navigation information, and environmental information and their associated parameter values and/or other attributes. The stored information is used by one or more analytics algorithms to segment the behaviors into operator or occupant profiles. Each profile segment is effectively a mapping of vehicle operation parameters (e.g., a value or range of values for steering angle, acceleration rate, deceleration rate, inter-vehicle distance, and the like) against sensed inputs, such as sensed occupant information, occupant information, navigation information, and/or environmental information, and descriptions and attributes in the stored information.

The profiles can be based on the behavioral observations for a specific occupant or set of occupants or for a specific type of occupant or set of occupants. The former profile generally does not include, in populating the profile, behaviors observed for different occupants or sets of occupants in other vehicles. The latter profile, by contrast, can include, in populating the profile, behaviors observed for different occupants or sets of occupants in other vehicles provide that the different occupants or sets of occupants are of a common type (e.g., cautious driver, aggressive driver, etc.). For example, if a first operator drives in Colorado and a second different operator drives in California, their values for vehicle parameters in response to different sensed input, such as sensed object information, vehicle-related information, navigation information and environmental information, can be merged to form a consolidated or aggregate profile that may be used to operate autonomously different vehicles for the different operators in the different states of Colorado and California. The driving behavior of the Colorado operator in snow can be used to operate autonomously for the California operator in the event that the California operator, for example, is in the vehicle under snowy or icy conditions (which are typically not experienced in many parts of California but are experienced in Colorado).

In an autonomous mode, the profile is ascertained based on an identity of the operator and occupants and the profile is then used to produce vehicle operation parameters in response to sensed object, navigation, and environmental information to operate the vehicle.

During capturing and storing of occupant information, vehicle parameters, sensed object information, vehicle-related information, navigation information, and environmental information, the captured and stored data is provided to the remotely profile database for analysis and profile generation and updating. The latency of data transmission is not typically an issue. During autonomous vehicle operation, however, the latency of profile receipt by the vehicle can be a concern due to the speed of the vehicle coupled with the limited sensor range. The latency issue can be addressed by identifying the appropriate profile(s) for the sensed occupants in the vehicle and providing the appropriate profile(s) to the vehicle in advance of autonomous operation. The profiles provided can be further filtered based on sensed object information, vehicle-related information, navigation information and/or environmental information (e.g., weather conditions).

In autonomous operations, profiles for types of sensed objects in proximity to the selected vehicle, such as animals (e.g., dogs, cats, geese, deer, and the like), children pedestrians, adult pedestrians, and vehicles and associated sensed occupants, can be provided to the vehicle by a profile database manager to enable more accurate behavior prediction of the sensed object type. The predicted behavior can be based on a parameter similar to the vehicle parameters, namely predicted angle of travel or direction of travel or movement, acceleration rate, deceleration rate, and inter-object distance (e.g., the distance the sensed object type will maintain relative to a nearby vehicle). For example, different vehicles can learn behaviors for different types of sensed objects in response to different sensed navigation and environmental information. This learned behavior can be merged into a profile for the corresponding type of object. When the type of object is sensed, the sensed navigation and/or environmental information can be used to select by mapping the predicted object behaviors.

Figure 8:
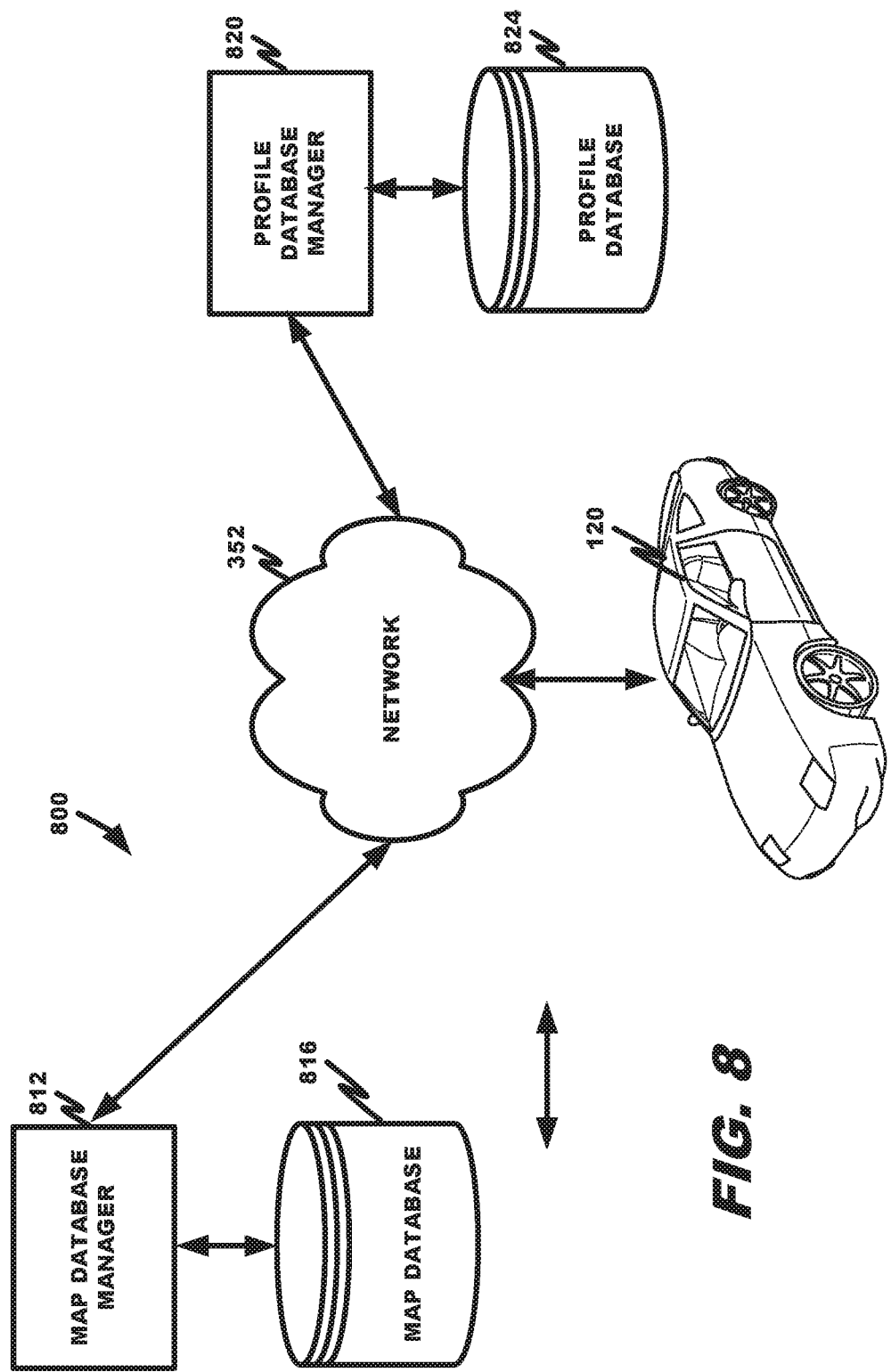
FIG. 8 is block diagram of a computational system in a vehicle and associated with one or more components described herein.
Figure 9:
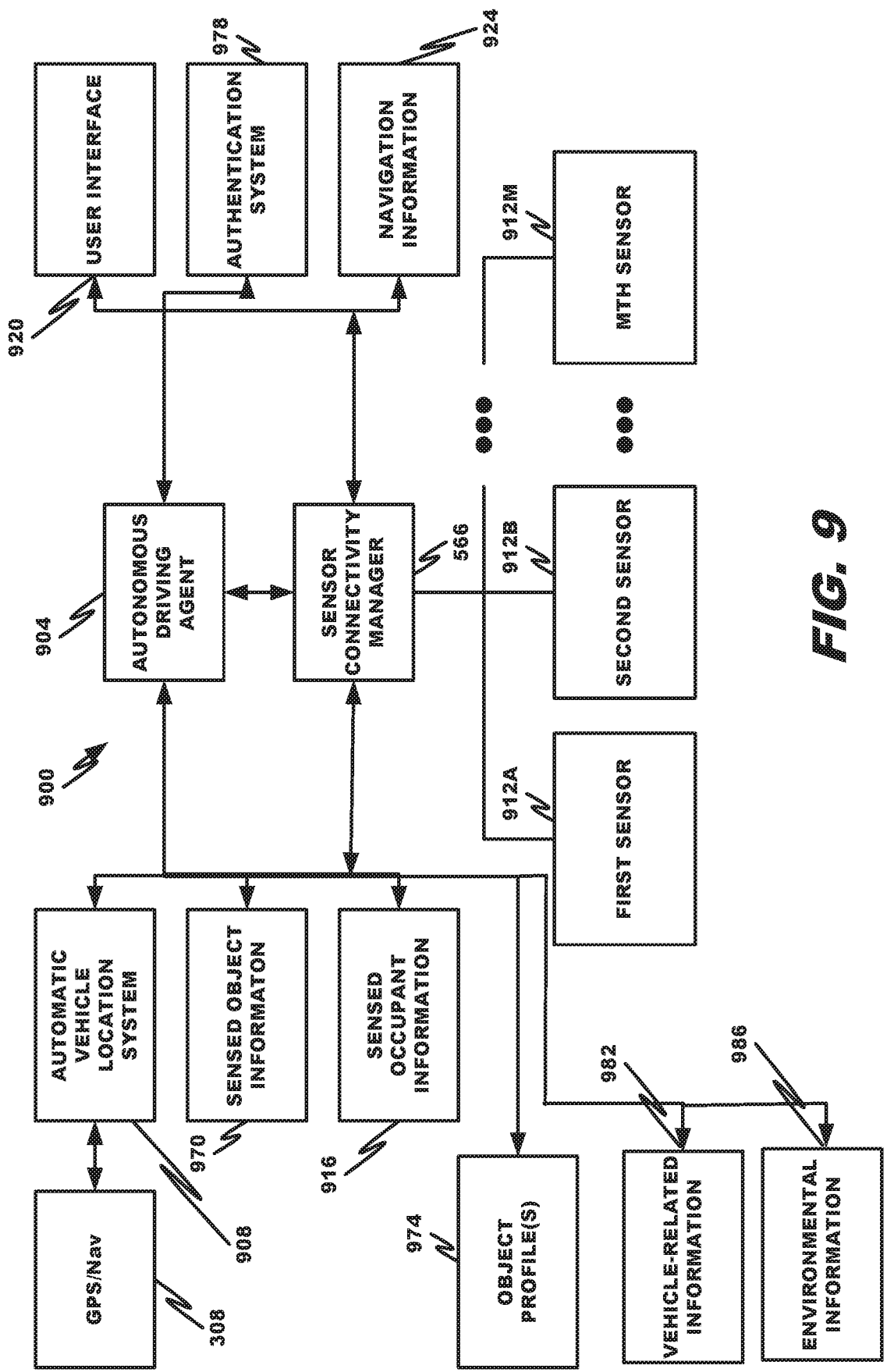
FIG. 9 is a block diagram of an autonomous driving vehicle system according to an embodiment.

With reference to FIGS. 3 and 8-9, the vehicle 100 is in wireless communication, via network 352, with navigation source 356A comprising a map database manager 812 and associated map database 816 and the control source 356B comprising a profile database manager 820 and associated profile database 824.

The map database manager 812 and map database 816 interact with the navigation sensor 308 (which is part of the automatic vehicle location system 908 discussed below) in the vehicle 100 to provide navigation or map output to an autonomous driving agent 904 in the vehicle 100.

The map database manager 812 stores and recalls navigation information from the map database 816.

The map database 816 contains navigation information in the form of maps. Maps are commonly stored as graphs, or two or three dimensional arrays of objects with attributes of location and category, where some common categories include parks, roads, cities, and the like. A map database commonly represents a road network along with associated features, with the road network corresponding to a selected road network model. Commonly, such a model comprises basic elements (nodes, links and areas) of the road network and properties of those elements (location coordinates, shape, addresses, road class, speed range, etc.). The basic elements are referred to as features and the properties as attributes. Other information associated with the road network can also be included, such as points of interest, waypoints, building shapes, and political boundaries. Geographic Data Files (GDF) is a standardized description of such a model. Each node within a map graph represents a point location of the surface of the earth and can be represented by a pair of longitude (lon) and latitude (lat) coordinates. Each link can represent a stretch of road between two nodes, and be represented by a line segment (corresponding to a straight section of road) or a curve having a shape that is generally described by intermediate points (called shape points) along the link. However, curves can also be represented by a combination of centroid (point or node), with a radius, and polar coordinates to define the boundaries of the curve. Shape points can be represented by longitude and latitude coordinates as are nodes, but shape points generally do not serve the purpose of connecting links, as do nodes. Areas are generally two- or three-dimensional shapes that represent things like parks The profile database manager 820 and profile database 824 interact with the autonomous driving agent 904 in each vehicle 100 to receive various types of information regarding vehicle behavior and the behaviors of nearby objects, such as other vehicles and pedestrians, generate individual and composite object profiles describing behavior of associated sets of objects (such as occupants of the vehicle or a nearby vehicle or a pedestrian), and provides the individual and composite object profiles to the vehicle 100 for use in determining and selecting various autonomous vehicle commands or settings, particularly acceleration rate of the vehicle, deceleration (e.g., braking) rate of the vehicle, steering angle of the vehicle (e.g., for turns and lane changes), and inter-object spacing (e.g., end-to-end or side-to-side spacing between the vehicle and a nearby object).

The profile database 824 containing the individual and composite object profiles 974 can be constructed according to any data model, whether conceptual, logical, or physical, such as a flat model, hierarchical model, network model, relational model, object-relational model, star schema, entity-relationship model, geographic model, generic model, semantic model, and the like.

Each object profile 974 generally contains multiple behavioral rules or behaviors and maps each behavioral rule or behavior against one or more sensed inputs to predict or cause behavior of a corresponding object. When a selected or predetermined set of sensed inputs is received, for example, the corresponding rule is implemented by the vehicle. The predetermined rules correspond to accelerate, acceleration rate, decelerate, deceleration rate, steering angle relative to a selected reference axis, and inter-object spacing magnitude (e.g., inter-vehicle spacing distance). In one example, each profile of an operator, occupant or group of occupants is composed of multiple profile segments. Each profile segment is a mapping of vehicle operational parameters (e.g., a value or range of values of a steering angle, acceleration rate, deceleration rate, and inter-vehicle distance) with respect to an object on the road, a navigation parameter, and/or environmental parameter. The profiles can be used with respect to one or more occupants of a selected vehicle or to predict behavior of nearby objects. In other words, the occupant profiles maintained by the profile database manager 820 can be used not only to select vehicle operations to be implemented by the selected vehicle but also to predict behaviors of occupants in nearby vehicles and the nearby vehicles themselves, which predicted behavior can be used in the selection of selected vehicle operations.

The sensed object information 970 can be information sensed by the first, second, . . . Mth sensors 912A-M regarding objects external to the vehicle 100. Examples of sensed object information 970 include animate objects and attributes thereof such as animals and attributes thereof (e.g., animal type, current spatial location, current activity, etc.), and pedestrians and attributes thereof (e.g., identity, age, sex, current spatial location, current activity, etc.), and the like and inanimate objects and attributes thereof such as other vehicles and attributes thereof (e.g., current vehicle state or activity (parked or in motion or level of automation currently employed), occupant or operator identity, vehicle type (truck, car, etc.), vehicle spatial location, etc.)), curbs and attributes thereof (topography and spatial location), potholes and attributes thereof (size and spatial location), lane division markers and attributes thereof (type or color and spatial locations), signage and attributes thereof (type or color and spatial locations such as speed limit signs, yield signs, stop signs, and other restrictive or warning signs), traffic signals and attributes thereof (e.g., red, yellow, blue, green, etc.), buildings and attributes thereof (spatial locations), walls and attributes thereof (height and spatial locations), and barricades and attributes thereof (height and spatial location).

The sensed occupant information 916 refers to information sensed by the first, second, . . . Mth sensors 912A-M regarding occupants in the selected vehicle 100. Examples of sensed occupant information comprises number and identities of occupants and attributes thereof (e.g., seating position, age, sex, gaze direction, biometric information, authentication information, preferences, historic behavior patterns (such as current or historical user driving behavior, historical user route, destination, climate control settings, and waypoint preferences), nationality, ethnicity and race, language preferences (e.g., Spanish, English, Chinese, etc.), occupant climate control preferences, current occupant role (e.g., operator or passenger), occupant priority ranking (e.g., vehicle owner is given a higher ranking than a child occupant), electronic calendar information (e.g., Outlook™), information displayed by portable computing devices within the vehicle 100 (such as destination and waypoints set in a navigation application), and medical information and history.

Vehicle-related information 982 can be any information sensed by the first, second, . . . Mth sensors 912A-M regarding the selected vehicle 100 itself. Examples include vehicle manufacturer, type, model, year of manufacture, current vehicle geographic location, current vehicle state or activity (parked or in motion or level of automation currently employed), vehicle specifications and capabilities, and currently sensed operational parameters for the vehicle (such as state of charge (SOC) or stored energy level of the energy storage unit).

Environmental information 986 can be any information sensed by the first, second, . . . Mth sensors 912A-M regarding the environment exterior to the selected vehicle 100. Examples include road type (pavement, gravel, brick, etc.), road condition (e.g., wet, dry, icy, snowy, etc.), current weather information (e.g., outside temperature, pressure, humidity, wind speed and direction, etc.), ambient light conditions (e.g., time-of-day), and degree of development of vehicle surroundings (e.g., urban or rural), and the like).

When a selected or predetermined set of sensed inputs is received, for example, with respect to another object, such as another vehicle operator or set of occupants or pedestrian, the corresponding rule or behavior can be predicted to be performed by the other object. The sensed inputs can vary by corresponding object type but include one or more of geographic or spatial vehicle location, sensed object information 970, sensed occupant information 916, selected vehicle-related information 982, exterior environmental information 986, occupant commands or other input, and other information. The occupant profile(s) 974 are normally attributed to the vehicle operator and the rules and corresponding stimulus or events are populated and/or updated by the autonomous driving agent 904 or profile database manager 820 as the occupant operates the vehicle.

Many techniques can be used by the profile database manager to create object profiles.

In one approach, the behavior of a given object or group of objects is predicted using one or more dynamic models, such as predictive analytics (e.g., predictive models, descriptive models, and decision models), among others. The approaches used to conduct predictive analytics include regression techniques, linear regression models, discrete choice models, logistic regression, multinomial logistic regression, probit regression, time series models, survival or duration analysis, classification and regression trees, multivariate adaptive regression splines, machine learning techniques, neural networks, multilayer perception, radial basis functions, support vector machines, Naïve Bayes, k-nearest neighbors, and geospatial predictive modeling. One specific example is the use of plural Kalman filters sequenced by a Markov chain.

In yet another approach, the behavior of a given object or group of objects is predicted using behavioral segmentation. Behavioral segmentation divides objects of a common type, e.g., drivers of different vehicles into groups or classes based on selected parameters of behavior, such as those set forth above.

There are two broad set of methodologies for segmentation: namely objective (supervised) and non-objective (unsupervised) segmentation methodologies. The most common techniques used for building an objective segmentation are CHAID and CRT. Each of these techniques attempts to maximize the difference among segments with regards to the stated objective or target for segmentation, which are the selected behavior parameters. CHAID uses a chi square statistic while CRT uses Gini impurity for the difference maximization. The most common techniques for building non-objective segmentation are cluster analysis and K nearest neighbor techniques. Each of these techniques uses a distance measure (e.g. Euclidian distance, Manhattan distance, or Mahalanobis distance). The distance measure maximizes the distance between the selected behavior parameters in the two segments.

In yet another approach, the behavior of a given occupant or group of occupants is predicted using occupant input on the selected parameters of behavior. The occupant input can be received by the user interface on board the vehicle.

When multiple occupants are in the vehicle, the autonomous driving agent 904 can blend individual profiles of each of the occupants to yield an aggregate or composite profile for use in any of the examples above. The composite profile recognizes that a given occupant's behavior when the occupant is alone is often different than the occupant's behavior when in a group. The composite profile for the group contains, in the occupant identity field, the identities of each of the occupants in the vehicle or occupant group. The role field, which defines the role of each individual participant in the behavior of the group on a group decision-by-decision basis or universally across all group decisions, contains a role value for each of the identified occupants. The role value indicates the degree of influence the corresponding occupant has over the behavior of the group. The occupant having the superior role value has a greater weighting assigned to that occupant's decision field values in each of various group decision or predictive behavior fields.

In yet another approach, the profile database manager constructs a composite profile based on observations of vehicle behavior while the occupant group members are in a common vehicle. The observed vehicle behavior is attributed to the group rather than to the operator. As the vehicle is operated with the occupant group in the vehicle, the various group profile field values are populated and/or updated.

When a given occupant is included in multiple composite profiles when he or she is in different occupant groups, the role and decision field values of the various composite profiles can be used to predict the given occupant's role value and decision field values of a different group of occupants containing different occupants besides the given occupant. This can be particularly true where the given occupant has a high or low role value consistently in the various composite values.

The navigation information 924 can take many forms depending on the configuration. When the navigation information 924 received by the vehicle from the automatic vehicle location system is provided, via network 352, to the map database manager 812, it can be the map or other navigation information provided by the map database manager 812 to the occupant, including possible routes and is periodically updated with selected route map information. When the navigation information is received by the automatic vehicle location system and used by the vehicle itself to configure, determine or select possible routes, it is map information from the map database 816 that is selected based on a requests received by the map database manager 812 from the vehicle 100. The request can include the current vehicle location and the locations of the user selected waypoints and destination.

With reference to FIG. 9, an on board autonomous driving system 900 in the vehicle 100 is depicted. The autonomous driving system 900 includes an autonomous driving agent 904 in communication with an automatic vehicle location system 908, sensor connectivity manager 566 and associated first, second, . . . Mth sensors 912a-M, user interface 920, and authentication system 978, and having access via working memory 736 or communication systems 728 to the sensed object information 970, sensed occupant information 916, object profiles 974, vehicle-related information 982, exterior environmental information 986, and navigation information 924.

The automatic vehicle location system 908 is in communication with the GPS/Nav sensor 308 to acquire current vehicle position coordinates, which position coordinates are then correlated by the map database manager 812 to a position on a road. Dead reckoning using distance data from one or more sensors attached to the drive train, a gyroscope sensor 312 and/or an accelerometer sensor 312 can be used for greater reliability, as GPS signal loss and/or multipath can occur due to the map database manager 812, such as due to a cellular signal dead or low signal strength area or passage of the vehicle through a tunnel.

The first, second, . . . mth sensors 912a-m can collect the sensed object information 970, sensed occupant information 916, vehicle-related information 982, and exterior environmental information 986. The first, second, . . . mth sensors 912a-m include the sensors or systems 116A-K, 112, 312, 316, 320, 324, 328, 332, 336, and 338 discussed above, a camera to capture images of interior objects (such as occupants), a seat belt sensor to determine seat belt settings (e.g., closed or open), a seat weight sensor settings, a microphone to capture audio within the vehicle (such as occupant comments which are then input into a speech-to-text engine to determine or identify one or more words spoken by an occupant), a wireless network node that receives unique identifiers of occupant portable computing devices (which identifiers can be associated with a corresponding occupant to identify the occupant), and the like. In some applications, a portable computing device of the occupant can be employed as a sensor that tracks occupant behavior while the occupant is in the vehicle. The information collected by the sensors is received by the sensor connectivity manager 566 and provided to the autonomous driving agent 904 and/or to the profile database manager.

The user interface 920 receives user commands and other input, such as user selections, preferences, and settings that are used in configuring, determining, and selecting vehicle parameters, settings, or operations, such as navigation route selection, acceptable rates of acceleration and deceleration, acceptable minimum inter-object spacing distance, and acceptable steering lines, and stimuli or events triggering associated rule-based actions. The user interface 920 can be one or more of vehicle instrument panel 400, vehicle operational display 420, heads-up display 434, and power management display 428. It can also be a portable computational or communication device of an occupant.

The authentication system 978 authenticates occupants using user selected credentials (e.g., password or personal identification number), a user computing device or keyfob emitted signal sequence or content (which sequence or content can be unique or substantially unique and therefore used to identify an associated user), and biometric physiological or behavioral information of the occupant, such as a fingerprint, palm vein pattern, facial characteristic, DNA sequence, palm print, hand geometry, iris characteristic, retina characteristic, odor/scent, occupant weight, and voice print or spectral characteristic. Behavioral biometric information includes seat settings, typing rhythm, and gait.

The autonomous driving agent 904 controls the driving behavior of the vehicle, specifically accelerate event, acceleration rate, decelerate event, deceleration rate, steering angle selected relative to a selected reference axis, and selected inter-object spacing magnitude in response to the current vehicle location, sensed object information 970, sensed occupant information 916, vehicle-related information 982, exterior environmental information 986, and navigation information 924 in accordance with the selected object profile(s) 974. In a typical implementation, the autonomous driving agent, based on feedback from certain sensors, specifically the LIDAR and radar sensors positioned around the circumference of the vehicle, constructs a three-dimensional map in spatial proximity to the vehicle that enables the autonomous driving agent to identify and spatially locate animate and inanimate objects. Other sensors, such as inertial measurement units, gyroscopes, wheel encoders, sonar sensors, motion sensors to perform odometry calculations with respect to nearby moving objects, and exterior facing cameras (e.g., to perform computer vision processing) can provide further contextual information for generation of a more accurate three-dimensional map. The navigation information is combined with the three-dimensional map to provide short, intermediate and long range course tracking and route selection. The autonomous driving system processes real-world information as well as GPS data, and driving speed to determine accurately the precise position of each vehicle, down to a few centimeters all while making corrections for nearby animate and inanimate objects.

The autonomous driving agent 904 processes in real time the aggregate mapping information and models behavior of occupants of the current vehicle and other nearby animate objects relying on the occupant profiles and profiles for the nearby animate objects. Occupant profiles for nearby animate objects can be selected by type of object, e.g., type of animal or pedestrian, and/or upon object identity. Object identity can be determined in many ways. For example, object identity can be determined by one vehicle transmitting an identity of one or more occupants to a nearby vehicle using a short range transmission protocol, a portable computing device of an occupant of another vehicle or pedestrian transmitting a unique identification signal (such as an electronic address) or occupant identification itself to the autonomous driving agent. Alternatively, the other vehicle can provide the object profile currently being used by its autonomous driving agent to control its driving operations to the autonomous driving agent of the selected vehicle. Alternatively, the profile database manager 820 can push the relevant object profiles to the autonomous driving agent based on the selected vehicle location and locations of nearby animate and inanimate objects. As more and more vehicles drive the selected route of the selected vehicle, sensor collected information of the vehicle can be provided in substantial real time to the map database manager 812 to enable it to generate a detailed three-dimensional map as the navigation information. This in effect uses each vehicle as a mapping information source to enable detailed and accurate three dimensional maps to be developed.

The autonomous driving agent, based on the occupant profiles and other object profiles, issues appropriate commands regarding implementing an accelerate event, acceleration rate, deceleration event, deceleration rate, inter-object spacing distance, and steering angle magnitude. While some commands are hard-coded into the vehicle, such as stopping at red lights and stop signs, other responses are learned and recorded by profile updates based on previous driving experiences. The learning ability of the autonomous driving agent updates not only the profiles related to the selected vehicle but also profiles of nearby objects. Examples of learned behavior include a slow-moving or stopped vehicle or emergency vehicle in a right lane suggests a higher probability that the car following it will attempt to pass, a pot hole, rock, or other foreign object in the roadway equates to a higher probability that a driver will swerve to avoid it, and traffic congestion in one lane means that other drivers moving in the same direction will have a higher probability of passing in an adjacent lane or by driving on the shoulder. The profile updates can be done locally in the vehicle or remotely by the profile database manager in response to data received from the selected and other vehicles.

The autonomous driving agent can be configured to handle other autonomous operations, regardless of automation level. Examples include adaptive cruise control, lane keeping, parking functions, and the like.

The operations of the various executable modules will now be discussed with reference to FIGS. 10-12.

Figure 10:
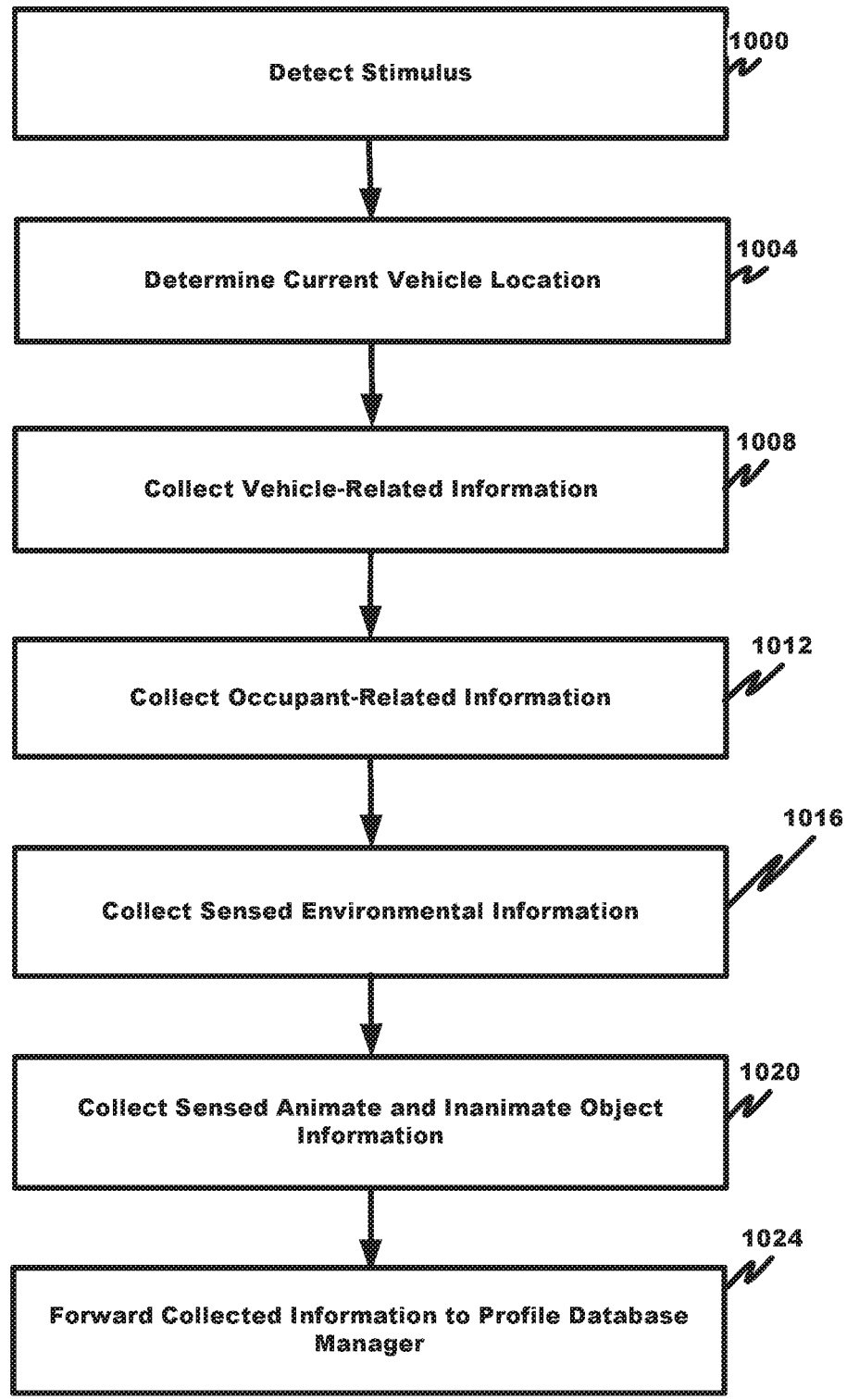
FIG. 10 is a flow chart associated with one or more embodiments presented herein.

With reference to FIG. 10, the autonomous driving agent 904, in step 1000, detects a stimulus, such as any set forth above, and commences execution of the instructions. Exemplary stimuli include, for example, detection of a change in any of the previously sensed vehicle location, sensed object information 970, sensed occupant information 916, vehicle-related information 982, exterior environmental information 986, and/or navigation information 924 and/or in an object profile(s) 974.

In step 1004, the autonomous driving agent 904 determines from the automatic vehicle location system 908 the current geographical location of the vehicle 100.

In step 1008, the autonomous driving agent 904 collects vehicle-related information 982 from the sensor connectivity manager 566.

In step 1012, the autonomous driving agent 904 collects occupant-related information 916, such as the information set forth above. This includes, for example, the identities of the vehicle occupants, the roles of each identified occupant (e.g., driver or passenger), a current activity of each occupant (e.g., operating vehicle, operating portable computing device, interacting with an on board vehicle user interface, and the like), gaze detection of an occupant, and the like.

In step 1016, the autonomous driving agent 904 collects sensed exterior environmental information 986 from the sensor connectivity manager 566.

In step 1020, the autonomous driving agent 908 collects sensed animate and inanimate object information 970 from the sensor connectivity manager 566.

In step 1024, the autonomous driving agent 908 forwards the foregoing collected information, via communications subsystem 350 and network 352, to the profile database manager 820 and map database manager 812.

Figure 11:
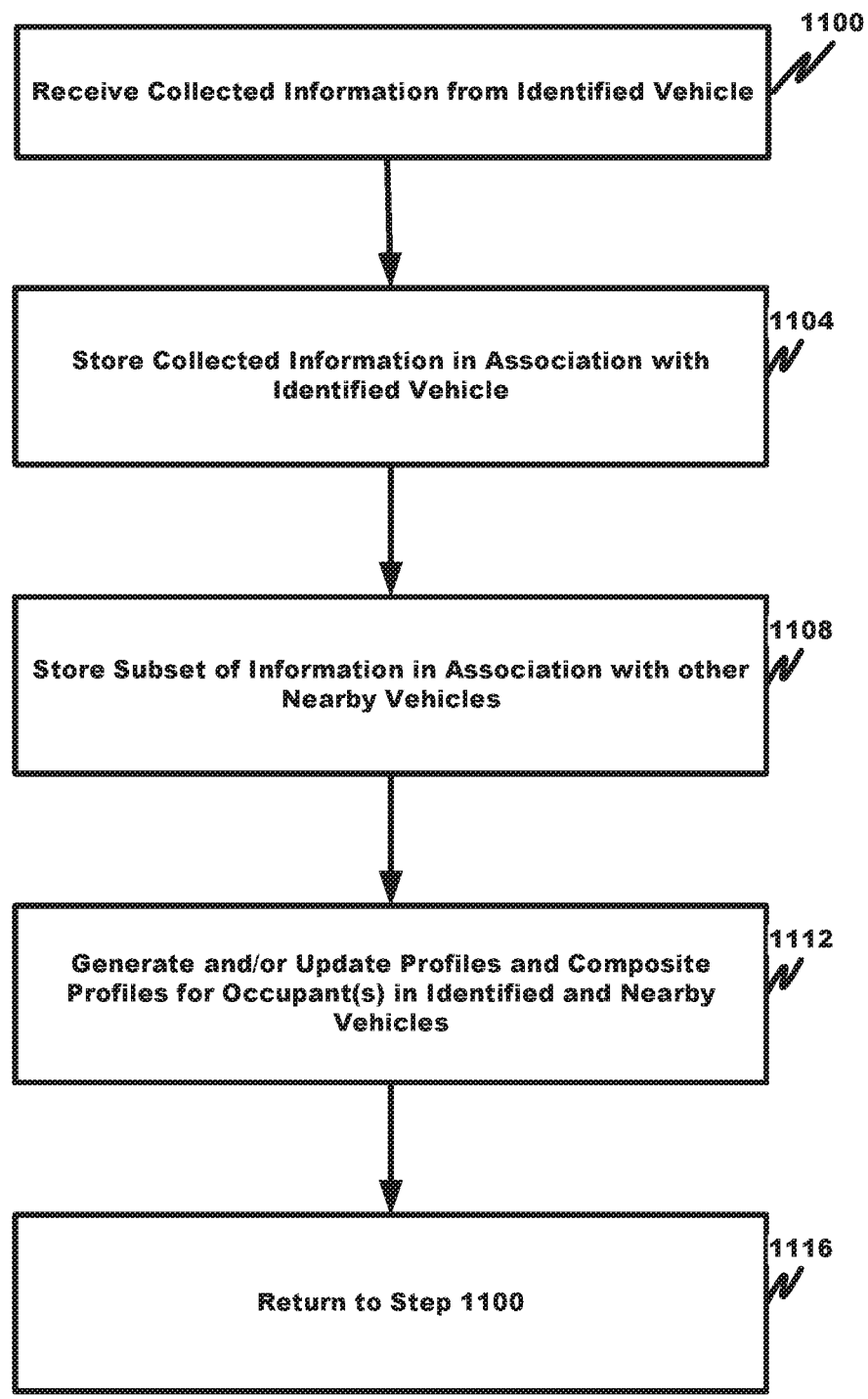
FIG. 11 is a flow chart associated with one or more embodiments presented herein.

With reference to FIG. 11, the profile database manager, in step 1100, receives the collected information from the autonomous driving agent of the selected vehicle along with a unique identifier of the vehicle (such as an identity of the owner, electronic address of the vehicle, serial number or vehicle identification number of the vehicle, and the like).

In step 1104, the profile database manager stores the collected information in the profile database along with the unique vehicle identifier and/or an identifier of an occupant of the vehicle 100.

In step 1108, the profile database manager stores a subset of the collected information in association with one or more other nearby objects, such as vehicles. The object behavioral observations of the selected vehicle of other spatially nearby objects can be used to update the profile of the spatially nearby object and vice versa.

In step 1112, the profile database manager updates profiles and composite profiles of objects, including occupants of the selected vehicle, both with respect to the selected vehicle and nearby objects observed by the selected vehicle.

In step 1116, the profile database manager returns to step 1100.

Figure 12:
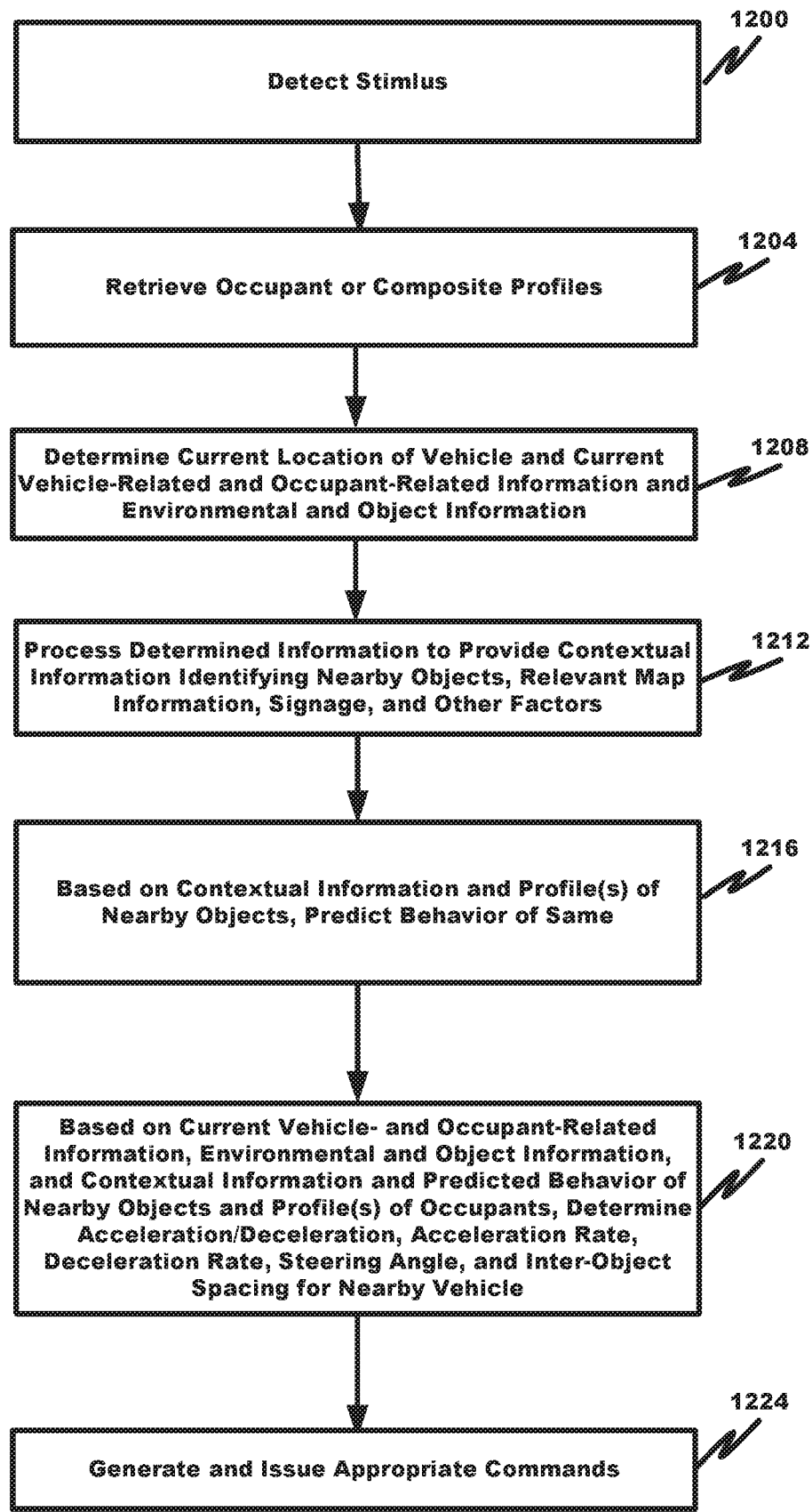
FIG. 12 is a flow chart associated with one or more embodiments presented herein.

With reference to FIG. 12, the autonomous driving agent 904, in step 1200, detects a stimulus, such as any set forth above, and commences execution of the instructions. Exemplary stimuli include, for example, detection of a change in any of the previously sensed vehicle location, sensed object information 970, sensed occupant information 916, vehicle-related information 982, exterior environmental information 986, and/or navigation information 924 and/or in an object profile(s) 974. Another stimulus is the vehicle transitioning to a higher level of automation, e.g., from Level 0 to Level 1, Level 1 to Level 2, Level 2 to Level 3, or Level 3 to Level 4.

In step 1204, the autonomous driving agent 904 retrieves or receives occupant or composite profiles regarding the occupants in the selected vehicle. The profiles can be stored, maintained and updated locally within the vehicle 100 or received, via the communications subsystem 350 and network 352, from the control source 356B.

In step 1208, the autonomous driving agent 904 determines from the automatic vehicle location system 908 a current location of the selected vehicle and receives from the sensor connectivity manager 966 current vehicle-related and occupant-related information 982 and 916 and exterior environmental and object information 986 and 970.

In step 1212, the autonomous driving agent 904 processes the determined information to provide contextual information identifying nearby objects, relevant map information, signage, and other factors.

In step 1216, the autonomous driving agent 904, based on the contextual information and profile(s) of nearby objects, predicts a behavior of the nearby objects.

In step 1220, the autonomous driving agent, based on current vehicle- and occupant-related information 982 and 916, exterior environmental and object information 986 and 970, and other contextual information and the predicted behavior of nearby objects and profile(s) of occupants, determines acceleration events, deceleration events, acceleration rate, deceleration rate, steering angle and inter-object spacing.

In step 1224, the autonomous driving agent then issues appropriate commands to other vehicle components, such as steering, braking, and throttle assemblies, to execute the determined instructions.

Figure 13:
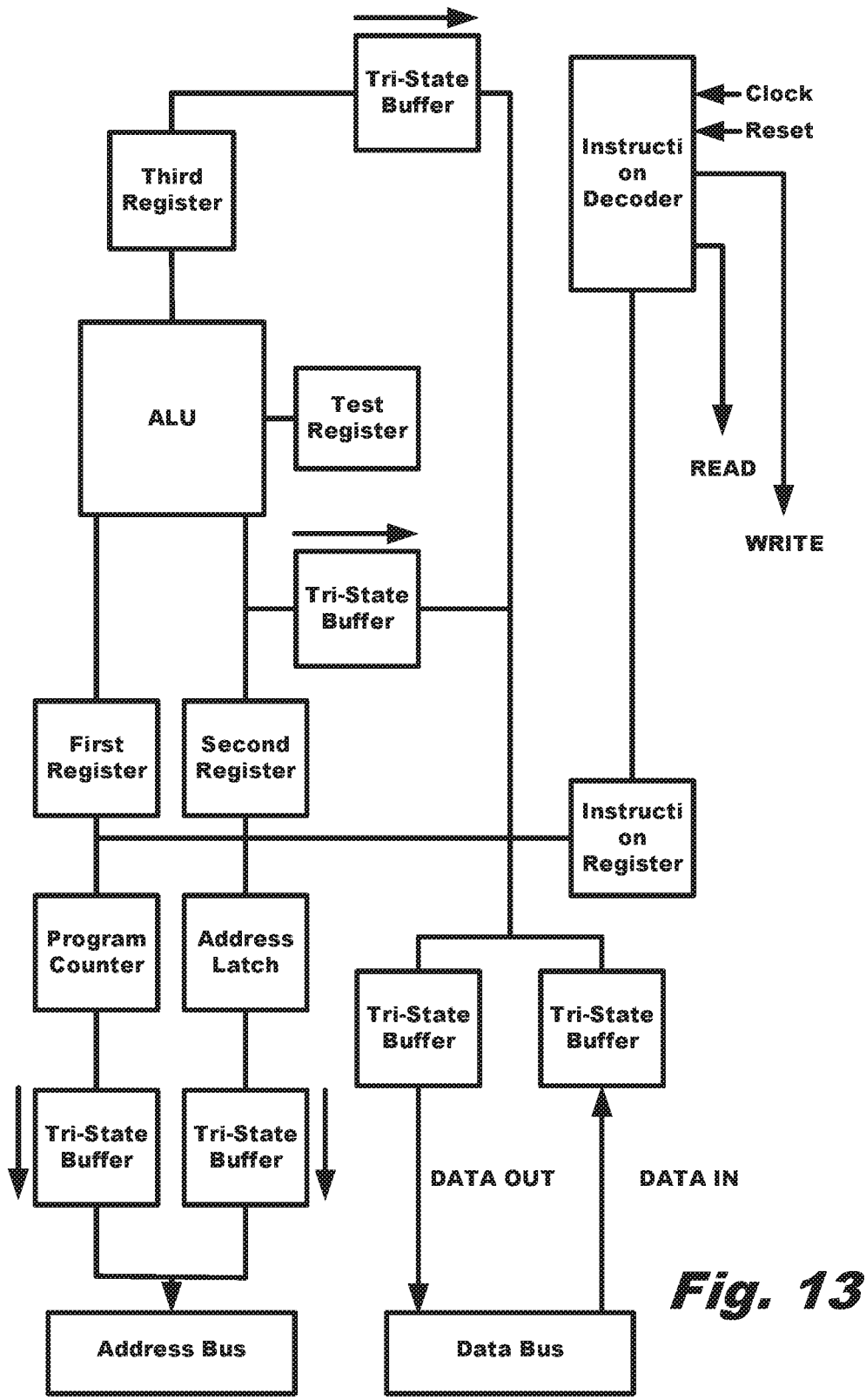
FIG. 13 is a block diagram of a computing system associated with one or more components described herein.

With reference to FIG. 13, the logical instructions are executed by an arithmetic/logic unit ("ALU"), which performs mathematical operations, such as addition, subtraction, multiplication, and division, machine instructions, an address bus (that sends an address to memory), a data bus (that can send data to memory or receive data from memory), a read and write line to tell the memory whether to set or get the addressed location, a clock line that enables a clock pulse to sequence the processor, and a reset line that resets the program counter to zero or another value and restarts execution. The arithmetic/logic unit can be a floating point processor that performs operations on floating point numbers. The autonomous driving agent 904, profile database manager 820, and/or map database manager 812 further includes first, second, and third registers that are typically configured from flip-flops, an address latch, a program counter (which can increment by "1" and reset to "0"), a test register to hold values from comparisons performed in the arithmetic/logic unit (such as comparisons in steps 1112, 1208, 1212, 1216, 1220, and 1224), plural tri-state buffers to pass a "1" or "0" or disconnect its output (thereby allowing multiple outputs to connect to a wire but only one of them to actually drive a "1" or "0" into the line), and an instruction register and decoder to control other components. Control lines, in the autonomous driving agent 904, profile database manager 820, and/or map database manager 812, from the instruction decoder can: command the first register to latch the value currently on the data bus, command the second register to latch the value currently on the data bus, command the third register to latch the value currently output by the ALU, command the program counter register to latch the value currently on the data bus, command the address register to latch the value currently on the data bus, command the instruction register to latch the value currently on the data bus, command the program counter to increment, command the program counter to reset to zero, activate any of the plural tri-state buffers (plural separate lines), command the ALU what operation to perform, command the test register to latch the ALU's test bits, activate the read line, and activate the write line. Bits from the test register and clock line as well as the bits from the instruction register come into the instruction decoder. Hardware similar or identical to that of FIG. 13 is in each of the autonomous driving agent 904, profile database manager 820 and/or map database manager 812 for executing the instructions of FIGS. 10-12. The ALU executes instructions for a random or pseudo-random number generation algorithm and generates the recipient identifier using the appropriate seed values.

Any of the steps, functions, and operations discussed herein can be performed continuously and automatically.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, sub-combinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments can include a vehicle comprising:

a vehicle interior for receiving one or more occupants;

a plurality of sensors to collect sensed information associated with the vehicle interior and an exterior of the vehicle;

an automatic vehicle location system to determine a current spatial location of the vehicle;

a computer readable medium to store one or more occupant profiles describing a behavioral response of the vehicle to the sensed information when the vehicle is in an autonomous mode of operation; and a microprocessor, coupled to the user interface, plurality of sensors, automatic vehicle location system, and computer readable medium, that, when in the autonomous mode of operation:

identifies a current occupant of the vehicle;

accesses an occupant profile corresponding to the identified occupant;

based on the occupant profile and the sensed information, selects one or more of an acceleration event, an acceleration rate, a deceleration event, a deceleration rate, a steering angle relative to a reference axis, and a spacing distance between an exterior surface of the vehicle and a nearby object; and causes the vehicle to execute the selected one or more of an acceleration event, an acceleration rate, a deceleration event, a deceleration rate, a steering angle relative to a reference axis, and a spacing distance between an exterior surface of the vehicle and a nearby object.

Embodiments can include a method that can include the steps:

identifying, by a microprocessor, a current occupant of a vehicle;

accessing, by the microprocessor, an occupant profile corresponding to the identified occupant;

based on the occupant profile and the sensed information, selecting, by the microprocessor, one or more of an acceleration event, an acceleration rate, a deceleration event, a deceleration rate, a steering angle relative to a reference axis, and a spacing distance between an exterior surface of the vehicle and a nearby object; and causing, by the microprocessor, the vehicle to execute the selected one or more of an acceleration event, an acceleration rate, a deceleration event, a deceleration rate, a steering angle relative to a reference axis, and a spacing distance between an exterior surface of the vehicle and a nearby object.

Embodiments can include a method that can include the steps:

identifying, by a microprocessor of a vehicle when operating in an autonomous driving mode, nearby object, the nearby object being one of an animal and human;

sensing, by the microprocessor, navigation and environmental information;

determining, by the microprocessor, a type of the identified nearby object;

accessing, by the microprocessor, a profile corresponding to the identified type of identified nearby object;

based on the accessed profile and one or more of the sensed navigation or environmental information, selecting, by the microprocessor, one or more of an acceleration rate, a deceleration rate, a direction of travel relative to a reference axis, and a spacing distance between an exterior surface of the vehicle and the identified nearby object, the one or more of an acceleration rate, a deceleration rate, a direction of travel relative to a reference axis, and a spacing distance between an exterior surface of the vehicle and the identified nearby object predicting a future behavior of the identified nearby object; and causing, by the microprocessor, the vehicle to execute an operation in response to the selected one or more of an acceleration rate, a deceleration rate, a direction of travel relative to a reference axis, and a spacing distance between an exterior surface of the vehicle and the identified nearby object to reflect the predicted future behavior of the identified nearby object.

Aspects of the above vehicle or method can include one or more of: the sensed information comprising navigation information, the navigation information comprising a dimensional array of features, each feature having an attribute of location and category, the occupant profile comprising behavioral responses and, for each behavioral response, sensed information triggering the corresponding behavioral response, the corresponding behavioral response being one or more of an acceleration event, an acceleration rate, a deceleration event, a deceleration rate, a steering angle relative to a reference axis, and a spacing distance between an exterior surface of the vehicle and a nearby object, and the sensed information comprising one or more of spatial vehicle location, sensed object information associated with objects in spatial proximity to the vehicle, sensed occupant information for the vehicle, selected vehicle-related information, exterior environmental information regarding an environment of the vehicle, and an occupant command.

Aspects of the above vehicle or method can include one or more of: the microprocessor accessing a profile of an object described in the sensed information, the object being another vehicle or a pedestrian, and the microprocessor's selection of the one or more of an acceleration event, an acceleration rate, a deceleration event, a deceleration rate, a steering angle relative to a reference axis, and a spacing distance between an exterior surface of the vehicle and a nearby object being based, at least in part, on the accessed object profile.

Aspects of the above vehicle or method can include one or more of: the microprocessor forwarding the sensed information to a remotely located profile database manager, the sensed information comprising a description of observed behavior of one or more nearby objects, and the profile database manager updating a profile for each of the one or more nearby objects based on the description of observed behavior.

Aspects of the above vehicle or method can include the microprocessor receiving an identifier of the other vehicle or pedestrian and uses the identifier to determine which object profile is to be accessed.

Aspects of the above vehicle or method can include the microprocessor or a remotely located profile database manager using the sensed information to update one or more fields of the one or more occupant profiles.

Aspects of the above vehicle or method can include one or more of: the vehicle comprising multiple occupants, each occupant having a corresponding occupant profile, the microprocessor combining parts of the occupant profiles to form a composite profile describing behavior for the multiple occupants, the microprocessor's selection of the one or more of an acceleration event, an acceleration rate, a deceleration event, a deceleration rate, a steering angle relative to a reference axis, and a spacing distance between an exterior surface of the vehicle and a nearby object being based, at least in part, on the composite profile, each of the occupant profiles being created by predictive analytics and/or behavioral segmentation, and the autonomous mode of operation being at least level 2 or higher.

Embodiments can include a method that can include the steps:

receiving, by a microprocessor, sensed information collected by a vehicle, the sensed information comprising a spatial location of the vehicle interior and describing an exterior environment of the vehicle, the exterior environment comprising one or more objects within a spatial range of the vehicle;

identifying, by the microprocessor, the one or more objects; and performing, by the microprocessor, one or both of the following:

(a) providing one or more behavioral profiles corresponding to the one or more objects to the vehicle to enable the vehicle to predict a behavior of the one or more objects and (b) updating one or more behavioral profiles corresponding to the one or more objects based on descriptive information in the sensed information regarding a sensed behavior of the one or more objects.

Aspects of the above vehicle or method can include one or more of: the one or more objects comprising a vehicle, the microprocessor performing (a), and the vehicle being an autonomous mode of operation.

Aspects of the above vehicle or method can include one or more of: the one or more objects comprising a vehicle and the microprocessor performing (b).

Aspects of the above vehicle or method can include the microprocessor selecting the one or more behavioral profiles based on spatial locations of the one or more objects received by the microprocessor from the one or more objects.

Aspects of the above vehicle or method can include one or more of: the one or more behavioral profiles comprising behavioral responses and, for each behavioral response, sensed information triggering the corresponding behavioral response, the corresponding behavioral response being one or more of an acceleration event, an acceleration rate, a deceleration event, a deceleration rate, a steering angle relative to a reference axis, and a spacing distance between an exterior surface of the object and a nearby object, and the sensed information comprising one or more of spatial object location, sensed object information associated with nearby objects, sensed occupant information for the object, selected object-related information, and exterior environmental information regarding an environment of the object.

Any one or more of the aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

The term "electric vehicle" (EV), also referred to herein as an electric drive vehicle, may use one or more electric motors or traction motors for propulsion. An electric vehicle may be powered through a collector system by electricity from off-vehicle sources, or may be self-contained with a battery or generator to convert fuel to electricity. An electric vehicle generally includes a rechargeable electricity storage system (RESS) (also called Full Electric Vehicles (FEV)). Power storage methods may include: chemical energy stored on the vehicle in on-board batteries (e.g., battery electric vehicle or BEV), on board kinetic energy storage (e.g., flywheels), and/or static energy (e.g., by on-board double-layer capacitors). Batteries, electric double-layer capacitors, and flywheel energy storage may be forms of rechargeable on-board electrical storage.

The term "hybrid electric vehicle" refers to a vehicle that may combine a conventional (usually fossil fuel-powered) powertrain with some form of electric propulsion. Most hybrid electric vehicles combine a conventional internal combustion engine (ICE) propulsion system with an electric propulsion system (hybrid vehicle drivetrain). In parallel hybrids, the ICE and the electric motor are both connected to the mechanical transmission and can simultaneously transmit power to drive the wheels, usually through a conventional transmission. In series hybrids, only the electric motor drives the drivetrain, and a smaller ICE works as a generator to power the electric motor or to recharge the batteries. Power-split hybrids combine series and parallel characteristics. A full hybrid, sometimes also called a strong hybrid, is a vehicle that can run on just the engine, just the batteries, or a combination of both. A mid hybrid is a vehicle that cannot be driven solely on its electric motor, because the electric motor does not have enough power to propel the vehicle on its own.

The term "rechargeable electric vehicle" or "REV" refers to a vehicle with on board rechargeable energy storage, including electric vehicles and hybrid electric vehicles.

What is claimed is:

1. A vehicle, comprising:
a vehicle interior for receiving a plurality of occupants;
a plurality of sensors to collect sensed information associated with the vehicle interior and an exterior of the vehicle;
an automatic vehicle location system to determine a current spatial location of the vehicle;
a computer readable medium to store one or more occupant profiles describing a behavioral response of the vehicle to the sensed information when the vehicle is in an autonomous mode of operation; and
a microprocessor, coupled to the plurality of sensors, automatic vehicle location system, and computer readable medium, that, when in the autonomous mode of operation:
identifies a first occupant of the vehicle;
accesses a first occupant profile corresponding to the identified first occupant, the first occupant profile comprising one or more behavior segments for the first occupant, the one or more behavior segments mapping a vehicle behavior response for the first occupant, the vehicle behavior response being one of more of an acceleration event, an acceleration rate, a deceleration event, a deceleration rate, a steering angle relative to a reference axis, and a spacing distance between an exterior surface of the vehicle and a nearby object for the first occupant, against one or more sensed inputs and wherein the vehicle collects sensed information during manual and autonomous control of the vehicle;
identifies a second occupant of the vehicle;
accesses a second occupant profile corresponding to the identified second occupant, the second occupant profile comprising one or more behavior segments for the second occupant;
determines, based on the sensed information collected while the first occupant and the second occupant are both in the vehicle, that at least one of the one or more behavior segments for the first occupant and the one or more behavior segments for the second occupant are different than when only one of the first occupant and the second occupant are in the vehicle;
generates, based on the first and the second occupant profiles and the determined difference in the at least one of the one or more behavior segments, a composite group profile comprising a combination of the first and the second occupant profiles that defines an autonomous control behavior for the one or more of an acceleration event, an acceleration rate, a deceleration event, a deceleration rate, a steering angle relative to a reference axis, and a spacing distance between an exterior surface of the vehicle and a nearby object in accordance with the combination of the first and the second occupant profiles;
selects the composite group profile for use by the vehicle while the first occupant and the second occupant are both in the vehicle; and
causes the vehicle to autonomously execute the selected one or more of an acceleration event, an acceleration rate, a deceleration event, a deceleration rate, a steering angle relative to a reference axis, and a spacing distance between an exterior surface of the vehicle and a nearby object in accordance with the composite group profile.

2. The vehicle of claim 1, wherein, when in the autonomous mode of operation, the microprocessor controls each of: the vehicle acceleration event, the vehicle acceleration rate, the vehicle deceleration event, the vehicle deceleration rate, the vehicle steering angle relative to a reference axis, and the spacing distance between an exterior surface of the vehicle and a nearby object, wherein the sensed information comprises navigation information, wherein the navigation information comprises a dimensional array of features, each feature having an attribute of location and category, wherein, for each vehicle behavioral response, predetermined sensed information triggers the corresponding behavioral response, and wherein the sensed information comprises one or more of spatial vehicle location, sensed object information associated with objects in spatial proximity to the vehicle, sensed occupant information for the vehicle, selected vehicle-related information, exterior environmental information regarding an environment of the vehicle, and an occupant command.

3. The vehicle of claim 1, wherein the microprocessor accesses a profile of an object described in the sensed information, wherein the object profile comprises one or more behavior segments, the one or more behavior segments mapping an object behavior response, the object behavior response being one of more of an acceleration event, an acceleration rate, a deceleration event, a deceleration rate, a steering angle relative to a reference axis, and a spacing distance between an exterior surface of the object and a nearby different object, against one or more sensed inputs in proximity to the object, wherein the object is another vehicle or a pedestrian, and wherein the microprocessor's selection of the one or more of an acceleration event, an acceleration rate, a deceleration event, a deceleration rate, a steering angle relative to a reference axis, and a spacing distance between an exterior surface of the vehicle and a nearby object is based, at least in part, on the accessed object profile.

4. The vehicle of claim 3, wherein the microprocessor or a remotely located profile database manager uses the sensed information to update one or more fields of the one or more occupant profiles and wherein the microprocessor receives an identifier of the other vehicle or pedestrian and uses the identifier to determine which object profile is to be accessed.

5. The vehicle of claim 1, wherein the one or more occupant profiles comprises behavior segments that are based on driving behaviors obtained from occupants of other vehicles having a characteristic in common with the first occupant.

6. The vehicle of claim 1, wherein the microprocessor forwards the sensed information to a remotely located profile database manager, wherein the sensed information comprises a description of observed behavior of one or more nearby objects, and wherein the profile database manager updates a profile for each of the one or more nearby objects based on the description of observed behavior.

7. The vehicle of claim 2, wherein the vehicle comprises multiple occupants, each occupant having a corresponding occupant profile, wherein the microprocessor combines parts of the occupant profiles to form the composite group profile describing behavior for the multiple occupants, wherein the microprocessor's selection of the one or more of an acceleration event, an acceleration rate, a deceleration event, a deceleration rate, a steering angle relative to a reference axis, and a spacing distance between an exterior surface of the vehicle and a nearby object is based, at least in part, on the composite group profile, wherein each of the occupant profiles is created by predictive analytics and/or behavioral segmentation.

8. A method, comprising:
identifying, by a microprocessor, a first occupant of a vehicle;

identifying, by the microprocessor, a second occupant of the vehicle;

when the microprocessor is in an autonomous mode of operation, accessing, by the microprocessor, a first occupant profile corresponding to the first identified occupant, the first occupant profile comprising one or more behavior segments for the first occupant, the one or more behavior segments mapping a vehicle behavior response for the first occupant, the vehicle behavior response being one of more of an acceleration event, an acceleration rate, a deceleration event, a deceleration rate, a steering angle relative to a reference axis, and a spacing distance between an exterior surface of the vehicle and a nearby object for the first occupant, against one or more sensed inputs, wherein the one or more behavior segments are based on sensed information collected by the vehicle during a manual vehicle control operation of the vehicle provided by the occupant, and accessing, by the microprocessor, a second occupant profile corresponding to the identified second occupant, the second occupant profile comprising one or more behavior segments for the second occupant;

determining by the microprocessor and based on the sensed information collected while the first occupant and the second occupant are both in the vehicle, that at least one of the one or more behavior segments for the first occupant and the one or more behavior segments for the second occupant are different than when only one of the first occupant and the second occupant are in the vehicle;

generating, by the microprocessor and based on the first and the second occupant profiles and the determined difference in the at least one of the one or more behavior segments, a composite group profile comprising a combination of the first and the second occupant profiles that defines an autonomous control behavior for one or more of an acceleration event, an acceleration rate, a deceleration event, a deceleration rate, a steering angle relative to a reference axis, and a spacing distance between an exterior surface of the vehicle and a nearby object in accordance with the combination of the first and the second occupant profiles;

selecting, by the microprocessor, the composite group profile for use by the vehicle while the first occupant and the second occupant are both in the vehicle, wherein the composite group profile is selected for use in place of a single one of the first occupant profile and the second occupant profile, and causing, by the microprocessor, the vehicle to autonomously execute the selected one or more of an acceleration event, an acceleration rate, a deceleration event, a deceleration rate, a steering angle relative to a reference axis, and a spacing distance between an exterior surface of the vehicle and a nearby object in accordance with the composite group profile.

9. The method of claim 8, wherein, when in the autonomous mode of operation, the microprocessor controls each of: the vehicle acceleration event, the vehicle acceleration rate, the vehicle deceleration event, the vehicle deceleration rate, the vehicle steering angle relative to a reference axis, and the spacing distance between an exterior surface of the vehicle and a nearby object, wherein the sensed information comprises navigation information, wherein the navigation information comprises a dimensional array of features, each feature having an attribute of location and category, wherein the vehicle collects sensed information during manual and autonomous control of the vehicle, wherein, for each vehicle behavioral response, predetermined sensed information triggers the corresponding behavioral response, and wherein the sensed information comprises one or more of spatial vehicle location, sensed object information associated with objects in spatial proximity to the vehicle, sensed occupant information for the vehicle, selected vehicle-related information, exterior environmental information regarding an environment of the vehicle, and an occupant command.

10. The method of claim 8, further comprising:
accessing, by the microprocessor, a profile of an object described in the sensed information, wherein the object profile comprises one or more behavior segments, the one or more behavior segments mapping an object behavior response, the object behavior response being one of more of an acceleration event, an acceleration rate, a deceleration event, a deceleration rate, a steering angle relative to a reference axis, and a spacing distance between an exterior surface of the object and a nearby different object, against one or more sensed inputs in proximity to the object, and wherein the object is another vehicle or a pedestrian, and wherein the microprocessor's selection of the one or more of an acceleration event, an acceleration rate, a deceleration event, a deceleration rate, a steering angle relative to a reference axis, and a spacing distance between an exterior surface of the vehicle and a nearby object is based, at least in part, on the accessed object profile.

11. The method of claim 10, wherein the microprocessor or a remotely located profile database manager uses the sensed information to update one or more fields of the one or more occupant profiles and wherein the microprocessor receives an identifier of the other vehicle or pedestrian and uses the identifier to determine which object profile is to be accessed.

12. The method of claim 8, wherein the one or more occupant profiles comprises behavior segments based on behaviors observed by another vehicle for a different occupant and wherein the one or more occupants and the different occupant have a common characteristic.

13. The method of claim 8, wherein the microprocessor forwards the sensed information to a remotely located profile database manager, wherein the sensed information comprises a description of observed behavior of one or more nearby objects, and wherein the profile database manager updates a profile for each of the one or more nearby objects based on the description of observed behavior.

14. The method of claim 9, wherein the composite group profile describes a driving behavior for additional occupants of the vehicle, wherein the microprocessor's selection of the one or more of an acceleration event, an acceleration rate, a deceleration event, a deceleration rate, a steering angle relative to a reference axis, and a spacing distance between an exterior surface of the vehicle and a nearby object is based, at least in part, on the composite group profile including the driving behavior for the additional occupants of the vehicle, wherein each of the occupant profiles is created by predictive analytics and/or behavioral segmentation.

15. A method, comprising:
receiving, by a microprocessor, sensed information collected by a vehicle, the sensed information comprising a spatial location of the vehicle and describing an exterior environment of the vehicle including one or more objects within a spatial range of the vehicle;
identifying, by the microprocessor, the one or more objects;

identifying, by the microprocessor, a first occupant of the vehicle;

accessing, by the microprocessor, a first occupant profile corresponding to the identified first occupant, the first occupant profile comprising one or more driving behavior segments for the first occupant;

providing, by the microprocessor, one or more behavioral profiles corresponding to the one or more objects to the vehicle to enable the vehicle to predict a behavior of the one or more objects;

updating, by the microprocessor, the one or more behavioral profiles corresponding to the one or more objects based on descriptive information in the sensed information regarding a sensed behavior of the one or more objects;

determining, by the microprocessor, a second occupant profile sharing a common driving type as the first occupant profile, the second occupant profile comprising one or more driving behaviors for the second occupant including an autonomous driving control response for the one or more objects when the first occupant profile is absent the autonomous driving control response for the one or more objects; and generating, by the microprocessor, a consolidated profile comprising a combination of the first and the second occupant profiles that autonomously controls the vehicle in accordance with the combination of the first occupant profile and the second occupant profile, and wherein the consolidated profile includes the autonomous driving control response for the one or more objects.

16. The method of claim 15, wherein the one or more objects comprises a vehicle, and wherein the vehicle is an autonomous mode of operation.

17. The method of claim 15, wherein the one or more objects comprises an animal.

18. The method of claim 16, wherein the microprocessor selects the one or more behavioral profiles based on spatial locations of the one or more objects received by the microprocessor from the one or more objects.

19. The method of claim 16, wherein the one or more behavioral profiles comprises behavioral responses for the object and, for each object behavioral response, sensed information triggering the corresponding object behavioral response, wherein the corresponding object behavioral response is one or more of an object acceleration event, an object acceleration rate, an object deceleration event, an object deceleration rate, an object steering angle relative to a reference axis, and a spacing distance between an exterior surface of the object and a nearby different object, and wherein the sensed information comprises one or more of spatial object location, sensed object information associated with nearby objects, sensed occupant information for the object, selected object-related information, and exterior environmental information regarding an environment of the object.

20. The method of claim 17, wherein the one or more behavioral profiles comprises behavioral responses for the object and, for each object behavioral response, sensed information triggering the corresponding behavioral response, wherein the corresponding object behavioral response is one or more of an object acceleration event, an object acceleration rate, an object deceleration event, an object deceleration rate, an object steering angle relative to a reference axis, and a spacing distance between an exterior surface of the object and a nearby different object, and wherein the sensed information comprises one or more of spatial object location, sensed object information associated with nearby objects, sensed occupant information for the object, selected object-related information, and exterior environmental information regarding an environment of the object.

21. A method, comprising:

identifying, by a microprocessor of a vehicle when operating in an autonomous driving mode, nearby object, the nearby object being one of an animal and human;

sensing, by the microprocessor, navigation and environmental information;

determining, by the microprocessor, a type of the identified nearby object;

accessing, by the microprocessor, a profile corresponding to the identified type of identified nearby object, the object profile comprises a behavioral response for the object and, for each object behavioral response, sensed information triggering the corresponding object behavioral response, wherein the corresponding object behavioral response is one or more of an object acceleration event, an object acceleration rate, an object deceleration event, an object deceleration rate, an object steering angle relative to a reference axis, and a spacing distance between an exterior surface of the object and a nearby different object;

based on the accessed profile and one or more of the sensed navigation or environmental information, predicting a future behavior of the identified nearby object;

identifying, by the microprocessor, a first occupant of a vehicle;

identifying, by the microprocessor, a second occupant of the vehicle;

accessing, by the microprocessor, a first occupant profile corresponding to the first identified occupant, the first occupant profile comprising one or more behavior segments for the first occupant, the one or more behavior segments mapping a vehicle behavior response for the first occupant against one or more sensed inputs, wherein the one or more behavior segments are based on sensed information collected by the vehicle during a manual vehicle control operation of the vehicle provided by the occupant;

accessing, by the microprocessor, a second occupant profile corresponding to the identified second occupant, the second occupant profile comprising one or more behavior segments for the second occupant;

determining, by the microprocessor, a composite group profile comprising a combination of the first and the second occupant profiles that defines an autonomous control behavior for the vehicle based on the combination of the first and the second occupant profiles;

selecting, by the microprocessor and based on the predicted future behavior of the identified nearby object and the composite group profile, one or more of a vehicle acceleration rate, a vehicle deceleration rate, a vehicle direction of travel relative to a reference axis, and a spacing distance between an exterior surface of the vehicle and the identified nearby object, the one or more of the vehicle acceleration rate, the vehicle deceleration rate, the vehicle direction of travel relative to a reference axis, and a spacing distance between an exterior surface of the vehicle and the identified nearby object in accordance with the composite group profile; and causing, by the microprocessor, the vehicle to autonomously execute an operation in response to the selected one or more of the vehicle acceleration rate, the vehicle deceleration rate, the vehicle direction of travel relative to a reference axis, and the vehicle spacing distance between an exterior surface of the vehicle and the identified nearby object to reflect the predicted future behavior of the identified nearby in accordance with the composite group profile.

\* \* \* \* \*

UNITED STATES PATENT AND TRADEMARK OFFICE
CERTIFICATE OF CORRECTION

PATENT NO. : 10,586,254 B2
APPLICATION NO. : 15/415650
DATED : March 10, 2020
INVENTOR(S) : Abhishek Singhal It is certified that error appears in the above-identified patent and that said Letters Patent is hereby corrected as shown below:

In the Claims

Claim 8, Column 37, Line 16, after "segments" insert --in the first occupant profile-- therein.
Claim 8, Column 37, Line 18, after "provided by the" insert --first-- therein.

Signed and Sealed this
Twelfth Day of May, 2020

Andrei Iancu
*Director of the United States Patent and Trademark Office*